US010369192B2

(12) United States Patent
Stern et al.

(10) Patent No.: US 10,369,192 B2
(45) Date of Patent: Aug. 6, 2019

(54) METHODS AND COMPOSITIONS FOR DELIVERY OF EXOGENOUS FACTORS TO NERVOUS SYSTEM SITES

(71) Applicant: REGENERATIVE RESEARCH FOUNDATION, Rensselaer, NY (US)

(72) Inventors: Sally Temple Stern, Slingerlands, NY (US); Natalia Lowry, Albany, NY (US); Jeffrey Stern, Slingerlands, NY (US); Susan K. Goderie, Ballston Spa, NY (US)

(73) Assignee: Regenerative Research Foundation, Rensselaer, NY (US)

( * ) Notice: Subject to any disclaimer, the term of this patent is extended or adjusted under 35 U.S.C. 154(b) by 0 days.

(21) Appl. No.: 14/078,329

(22) Filed: Nov. 12, 2013

(65) Prior Publication Data

US 2014/0227232 A1    Aug. 14, 2014

Related U.S. Application Data

(63) Continuation of application No. 13/108,552, filed on May 16, 2011, now abandoned, which is a continuation of application No. 12/398,888, filed on Mar. 5, 2009, now abandoned.

(60) Provisional application No. 61/034,068, filed on Mar. 5, 2008.

(51) Int. Cl.
| | | |
|---|---|---|
| *A61K 35/30* | (2015.01) | |
| *A61K 38/18* | (2006.01) | |
| *A61K 9/19* | (2006.01) | |
| *A61K 38/17* | (2006.01) | |
| *A61K 9/00* | (2006.01) | |
| *C12N 5/0797* | (2010.01) | |

(52) U.S. Cl.
CPC ........ *A61K 38/1709* (2013.01); *A61K 9/0019* (2013.01); *A61K 9/19* (2013.01); *A61K 35/30* (2013.01); *A61K 38/18* (2013.01); *C12N 5/0623* (2013.01)

(58) Field of Classification Search
None
See application file for complete search history.

(56) References Cited

U.S. PATENT DOCUMENTS

| | | | |
|---|---|---|---|
| 4,298,822 | A | 11/1981 | Fukuda |
| 5,356,635 | A | 10/1994 | Raman et al. |
| 6,165,747 | A | 12/2000 | Ingham et al. |
| 6,271,363 | B1 | 8/2001 | Ingham et al. |
| 6,337,539 | B1 | 1/2002 | Yorifuji et al. |
| 6,664,075 | B2 | 12/2003 | Ingham et al. |
| 7,226,617 | B2 | 6/2007 | Ding et al. |
| 2002/0057059 | A1 | 5/2002 | Ogishi et al. |
| 2003/0134414 | A1 | 7/2003 | Ferguson |
| 2003/0220280 | A1 | 11/2003 | Bunge et al. |
| 2005/0095706 | A1 | 5/2005 | Zhang et al. |
| 2005/0208545 | A1 | 9/2005 | Beachy |
| 2005/0277189 | A1 | 12/2005 | Temple et al. |
| 2006/0069009 | A1 | 3/2006 | Messina et al. |
| 2006/0182724 | A1 | 8/2006 | Riordan |
| 2007/0254842 | A1 | 11/2007 | Bankiewicz |

FOREIGN PATENT DOCUMENTS

WO    WO1993010758 A1    6/1993

OTHER PUBLICATIONS

Bambakidis et al. (The Spine J 4:16-26, 2004).*
Anderson et al (Advanced Drug Del Rev 28: 5-24, 1997).*
Varde et al (Expert Opin Biol Ther 4: 35-51, 2004).*
Bambakidis et al (J Neurosurg 99: 70-75, 2003) (abstract only).*
Marigo, V., et al. "Biochemical evidence that Patched is the Hedgehog receptor", Nature 384, pp. 176-179, (1996).
Marti, E., et al., "Requirement of 19K form of Sonic hedgehog for induction of distinct ventral cell types in CNS explants" Nature vol. 375, pp. 322-325 (1995).
Freiberg et al., "Polymer Microspheres for controlled drug release", International J. of Pharmaceutics (2004) 282:1-18.
Berkland et al., "PLG Microsphere Size Controls Drug Release Rate Through Several Competing Factors", Pharm. Res. (2003), 20:1055-1062.
Storkebaum E. et al., Treatment of motoneuron degeneration by intracerebroventricular delivery of VEGF in a rat model of ALS, Nat. Neurosci. Jan. 2005; 8(1 ):85-92. Epub Nov. 28, 2004.
Hashimoto et al., "Neuroprotective effect of sonic hedgehog up-regulated in Schwann cells following sciatic nerve injury", J. Neurochem. Nov. 2008; 107(4):918-27. Epub Sep. 11, 2008.
Xu QG, et al. "Facilitated sprouting in a peripheral nerve injury", Neuroscience, Apr. 9, 2008; 152(4):877-87. Epub Feb. 15, 2008.
Merchan et al., "Sonic hedgehog promotes the migration and proliferation of optic nerve oligodendrocyte precursors", Mol Cell Neurosci. Nov. 2007; 36(3):355-68. Epub Aug. 1, 2007.
Mastronardi et al., "The amount of sonic hedgehog in multiple sclerosis white matter is decreased and cleavage to the signaling peptide is deficient", Mult Scler Aug. 2003; 9(4):362-71.
Sun et al., "Olig bHLH proteins interact with homeodomain proteins to regulate cell fate acquisition in pregenitors of the ventral neural tube", Curr Bioi Sep. 18, 2001; 11 (18):1413-20.
Yang et al., "Endogenous neurogenesis replaces oligodendrocytes and astrocytes after primate spinal cord injury", J Neurosci Feb. 22, 2006;26(8):2157-66.

(Continued)

*Primary Examiner* — Gregory S Emch
*Assistant Examiner* — Aditi Dutt
(74) *Attorney, Agent, or Firm* — Fish & Richardson P.C.

(57) ABSTRACT

The present invention relates to treatment methods and methods for sustained delivery of one or more exogenous factors to desired nervous system sites. In certain embodiments, the invention relates to the use of biodegradable microspheres to deliver exogenous factors, such as the morphogenic factor, sonic hedgehog (Shh), to the site of spinal cord injury. In certain embodiments, the Shh-releasing microspheres are administered together with stem cells, which may be spinal cord neural stem cells. In certain embodiments, the invention relates to regrowth of neural cells in both the central and peripheral nervous systems.

10 Claims, 9 Drawing Sheets

Specification includes a Sequence Listing.

(56) References Cited

OTHER PUBLICATIONS

Shihabuddin et al., "Adult spinal cord stem cells generate neurons after transplantation in the adult dentate gyrus", J Neurosci Dec. 1, 2000 ;20(23):8727-35.
Horner et al., "Proliferation and differentiation of progenitor cells through the intact adult rat spinal cord", J Neurosci Mar. 15, 2000;20(6):2218-28.
Uchida et al.. "Direct isolation of human central nervous system stem cells". Proc Natl Acad Sci USA Dec. 19, 2000;97 (26):14720-5.
Struve et al.. "Disruption of the hyaluronan-based extracellular matrix in spinal cord promotes astrocyte proliferation". Glia Oct. 2005;52(1): 16-24.
Metz, G. A. And I. Q. Whishaw, "Cortical and subcortical lesions impair skilled walking in the ladder rung walking test: a new task to evaluate fore- and hindlimb stepping, placing, and co-ordination." J Neurosci Methods 115(2): 169-79. (2002).
Myers, Eugene and Webb Miller, "Optimal alignments in linear space" CABIOS vol. 4 pp. 11-17 (1988).
Needleman and Wunsch "A General Method Applicable to the Search for Similarities in the Amino Acid sequence of Two Pro-teins" J. Mol. Biol. vol. 48:444-453 (1970).
Newman, KD. et al., "Poly(D, L lactic-co-glycolic acid) microspheres as biodegradeable microcarriers for pluripotent stem cells", Biomateri-als; 25, pp. 5763-5771, (2004).
Novikov LN, Novikova LN, Mosahebi A, Wiberg M, Terenghi G, Kellerth JO "A novel biodegradable implant for neuronal rescue and regeneration after spinal cord injury" Biomaterials 23(16):3369-76 (2002).
Novikov LN, Novikov LN, Kellerth JO "Biopolymers and biode-gradable smart implants for tissue regeneration after spinal cord injury" Curr Opin Neurol.16(6):711-715, (2003).
Ono et ai, "Differences in neurogenic potential in floor plate cells along an anteroposterior location: midbrain dopaminergic neurons orginate from mesencephalic floor plate cells", Development and Disease, vol. 134 pp. 3213-3125, (2007).
Palma, V., D. A. Lim, N. Dahmane, P. Sanchez, T. C. Brionne, C. D. Herzberg, Y. Gitton, A. Carleton , A. Alvarez-Buylla and A. Ruiz i Altaba "Sonic hedgehog controls stem cell behavior in the post-natal and adult brain." Development 132 (2): 335-344, (2005).
Parisi et al., "The role of the hedgehog/patched signaling pathway in epithelial stem cell proliferation: from fly to human" Cell Res 8, pp. 15-21, (1998).
Park, E., A. A. Velumian and M. G. Fehlings. "The role of excitotoxicity in secondary mechanisms of spinal cord injury: a review with an emphasis on the implications for white matter degeneration" J Neurotrauma 21(6): 754-774, (2004).
Pearse DO, Bunge MB, "Designing cell- and gene-based regenera-tion strategies to repair the injured spinal cord", J. Neurotrauma vol. 23(3-4):438-52 (2006).
Perrimon, N., "Hedgehog and Beyond", Cell 80:517-520(1995).
Piantino et aL "An injectable, biodegradeable hydrogel for trophic factor delivery enhances axonal rewiring and improves performance after spinal cord injury" Exp. NeuroL, Oct 201(2):359-367, (2006).
Porter, JA et aL "The product of hedgehog autoproteolytic cleavage active in local and long-range signaling", Nature pp. 374:363-366, (1995).
Porter, JA et aL "Cholesterol Modification of Hedgehog Signaling Proteins in Animal Development" Science 274:255-259, (1996).
Qian, x., A. A. Davis, S. K. Goderie and S. Temple, "FGF2 concentration regulates the generation of neurons and glia from multipotent cortical stem cells" Neuron 18(1): 81-93 (1997).
Reeck et al., "Homology" in Proteins and Nucleic Acids "A Terminology Muddle and a Way out of it" Cell; vol. 50: pp. 667 (1987).
Rochkind S,et aL "Development of a tissue-engineered composite implant for treating traumatic paraplegia in rats." Eur Spine J. vol. 15(2):234-45, (2006).

Roelink et ai, "Floor Plate and Motor Neuron Induction by Different Concentrations of the Amino-Terminal Cleavage Product of Sonic Hedgehog Autoproteolysis" Cell 81 :445-455, (1995).
Schwab JM, et aL "Experimental strategies to promote spinal cord regeneration—an integrative perspective" Prog. NeurobioL 78(2):91-116, (2006).
Silver, J. And J. H. Miller "Regeneration beyond the glial scaL" Nat Rev Neurosci 5(2):146-56, (2004).
Simmons, CA et al. "Dual growth factor delivery and controlled scaffold degradation enhance in vivo bone formation by trans-planted bone marrow stromal cells" Bone; 35:562-569, (2004).
Smith RR, et al. "The Louisville Swim Scale: A Novel Assessment of Hindlimb Function following Spinal Cord Injury in Adult Rats", J Neurotrauma. vol. 11 pp. 1654-1670, (2006).
So, P. L, et al."Interactions between retinoic acid, nerve growth factor and sonic hedgehog signalling pathways in neurite out-growth" Dev Bioi vol. 298 pp. 167-175, (2006).
St. Jacques et al., "Sonic hedgehog signaling is essential for hair development", Current Biology, 8, pp. 1058-1068 (1998).
Stone, D. M., et al. "The tumour-suppressor gene patched encodes a candidate receptor for Sonic hedgehog", Nature 384,129-134, (1996).
Taylor et al., Soc Neurosc, Abstract No. 880.7, 2003.
Takebayashi et al. "The Basic Helix-Loop-Helix Factor Olig is Essential for the Development of Motoneuron and Oligodendrocyte Lineages" Current Biology vol. 12, 1157-1163, (2002).
Taylor et al., "Enhanced Potency of Human Sonic Hedgehog by Hydropphobic Modification" Biochemistry. Apr. 10;40 (14):4359-71, (2001).
Tekki-Kessaris, N., R. Woodruff, A. C. Hall, W Gaffield, S. Kimura, C. D. Stiles, D. H. Rowitchand W D. Richardson, "Hedgehog-dependent oligodendrocyte lineage specification in the telencephalon." Development 128{13):pp. 2545-2554, (2001).
Therond, P. P., et al. "Phosphorylation of the fused protein kinase in response to signaling from hedgehog", Proc. Natl. Acad. Sci. USA 93, pp. 4224-4228, (1996).
Thuret, S., L D. Moon and F. H. Gage, "Therapeutic interventions after spinal cordinjury." Nat Rev Neurosci 7(8): 628-43, (2006).
Vallieres, N., J. L Berard, S. David and S. Lacroix "Systemic injections of lipopolysaccharide accelerates myelin phagocytosis during Wallerian degeneration in the injured mouse spinal cord" Glia 53(1) pp. 103-113, (2006).
Zhou and Anderson, "The bHLH Transcription Factors OLIG2 and OLIG1 Couple Neuronal and Glial Subtype Specification", Cell, vol. 109:61-73 (2002).
Zhu et al. Stabilization of proteins encapsulated in injectable poly (lactide-co-glycolide), Nature Biotech, vol. 18 (1 ):52-57, (2000).
Sinha and Trehan J Control Rei 90: 261-280, 2003.
Pepinsky et al. (Jour Pharm Sci 91: 371-387, 2002).
Agius, E., C. Soukkarieh, C. Danesin, P. Kan, H. Takebayashi, C. Soula and P. Cochard, "Converse control of oligodendrocyte and astrocyte lineage development by Sonic hedgehog in the chick spinal cord." Dev Bioi 270 (2):308-21, (2004).
Ahn S, Joyner Alexander, "In vivo analysis of quiescent adult neural stem cells responding to Sonic hedgehog" Nature. vol. 437, pp. 894-897 (2005).
Akazawa, C., H. Tsuzuki, Y. Nakamura, Y. Sasaki, K. Ohsaki, S. Nakamura, Y. Arakawa and S. Kohsaka "TheUpregulated Expres-sion of Sonic Hedgehog in Motor Neurons After Rat Facial Nerve Axotomy." J Neurosci 24 (36): 7923-30, (2004).
Alcedo, J., et al. "The *Drosphila* smoothened Gene Encodes a Seven-Pass Membrane Protein, a Putative Receptor for the Hedge-hog Signal" Cell 86, pp. 221-232, (1996).
Alexandre, C., et al. "Transcriptional activation of hedgehog target genes in *Drosophila* is mediated directly by the Cubitus interruptus protein, a member of the GLI family of zinc finger DNA-binding proteins" Genes & Dev. 10, pp. 2003-2013(1996).
Altschul et al., "Gapped Blast and PSI-BLAST: a new generation of protein database search programs" Nucleic Acids Res., 25:3389-3402 (1997).
Altschul et al., "Basic Local Alignment Search Tool". J. Mol. Biol.; 215, pp. 403-410, (1990).
Ashton, R S.; Banerjee, A.; Punyani, S.; Schaffer, D. V.; Kane, R S. (2007) "Scaffolds based on Degradable Alginate Hydrogels and

(56) References Cited

OTHER PUBLICATIONS

Poly (lactide-co-glycolide) Microspheres for Stem Cell Culture." Biomaterials, 28, pp. 5518-5525. (2007).
Azanchi R, Bernal G., Gupta R, Keirstead HS. "Combined demyelination puis Schwann cell transplantation therapy increases spread of cells and axonal regeneration following contusion injury", J. Neurotrauma, vol. 21 No. 6 pp. 775-788 (2004).
Bambakidis, N. C. and R H. Miller "Transplantation of oligodendrocyte precursors and sonic hedgehog results in improved function and white matter sparing in the spinal cords of adult rats after contusion." Spine J 4(1) pp. 16-26 (2004).
Basso, D. M., L. C. Fisher, A. J. Anderson, L B. Jakeman, D. M. McTigue and P. G. Popovich "Basso Mouse Scale for locomotion detects differences in recovery after spinal cord injury in five common mouse strains." J Neurotrauma 23 (5): 635-59 (2006).
Bretzner F, Lui, J.,Currie E., Roskams AJ, TetzlaffW "Undesired effects of a combinatorial treatment for spinal cord injury—transplantation of olfactory ensheathing cells and BDNF infusion to the red nucleus" Eur. J. Neurosci; 28(9) pp. 1795-1807 (Nov. 2008).
Cao et ai, "Delivering neuroactive molecules from biodegradeable microspheres for application in central nervous system disorders", Biomaterials, Feb;20(4),pp. 329-339, (1999).
Cattaneo, E. M., R "Proliferation and differentiation of neuronal stem cells regulated by nerve growth factor." Nature 347:762-765, (1990).
Charron, F., E. Stein, J. Jeong, A. P. McMahon and M. Tessier-Lavigne (2003). "The morphogen sonic hedgehog is an axonal chemoattractant that collaborates with netrin-1 in midline axon guidance" Cell, vol. 113:11-23.
Charytoniuk D, Porcel B, Rodriguez Gomez J, Faure H, Ruat M, Traiffort E "Sonic Hedgehog signalling in the developing and adult brain" Journal of Physiology, Paris 96, pp. 9-16 (2002).
Chen, J., S. Y. Leong and M. Schachner "Differential expression of cell fate determinants in neurons and glial cells of adult mouse spinal cord after compression injury" Eur J Neurosci 22(8:1895-906, (2005).
Dahmane et al., Activation of the transcription factor Gli 1 and the Sonic hedgehog signaling pathway in skin tumours, Nature, 389, 876-880 (1997).
Danesin C, et al. Ventral Neural Progenitors Switch toward an Oligodendroglial Fate in Response to Increased Sonic Hedgehog (Shh) Activity: Involvement of Sulfatase 1 in Modulating Shh Signaling in the Ventral Spinal Cord, J Neurosci.; 26(19):5037-48 (2006).
Dominguez, M., et al. "Sending and Receiving the Hedgehog Signal: Control by the *Drosophila* Gli Protein Cubitus interruptus" Science vol. 272, 1621-1625 (1996).
Drury, J.L. et al. "Hydrogels for tissue engineering: scaffold design variables and applications" Biomaterials; 24:4337-4351 (2003).
Ekker, S. C. et al. "Distinct expression and shared activities of members of the hedgehog gene family of Xenopus laevis" Development 121:2337-2347, (1995).
Eldridge, J.H. et al. "Biodegradeable and Biocompatible Poly{DL-Lactaide-Co-Glycolide) Microspheres as an Adjuvant for *Staphylococcal* Enterotoxin B Toxoid Which enhances the levels of Toxin-Neurtalizing Antibodies" Infection and Immunity; 59(9):2978-2986, (1991).
Enzmann, G. U., R. L. Benton, J. F. Talbott, Q. Cao and S. R. Whittemore "Functional considerations of stem cell transplantation therapy for spinal cord repair" J Neurotrauma 23(3-4): 479-95 (2006).
Ericson et ai, "Pax6 Controls Progenitor Cell Identity and Neuronal Fate in Response to Graded Shh Signaling" Cell; 90{1 ):169-180,(1997).
Fan, C.-M. et al. "Long-Range Sclerotome Induction by Sonic Hedgehog: Direct Role of the Amino-Terminal Cleavage Product and Modulation by the Cyclic AMP Signaling Pathway" Cell 8:457-465, (1995).
Fietz, M. J. et ai, "Secretion of the amino-terminal fragment of the Hedgehog protein is necessary and sufficient for hedgehog signaling in *Drosphilia", Drosophila*.Curr. Biol. 6:643-650 . (1995).
Forbes, A. J. et al. "Hedgehog is required for the proliferation and specification of ovarian somatic cells prior to egg chamber formation in *Drosophila*", Development 122:112;5(1996).
Frank-Kamenetsky M, Zhang XM, Bottega S, Guicherit 0, Wichterle H, Dudek H, Bumcrot D, Wang FY, Jones S, Shu 10k J, Rubin LL, Porter JA ,"Small-molecule modulators of Hedgehog signaling: identification and characterizationof Smoothened agonists and antagonists." J Biol. Nov. 6;1(2):10 (2002).
Fu K, Harrell R, Zinski K, Um C, Jaklenec A, Frazier J, Lotan N, Burke P, Klibanov AM, Langer R. "A potential approach for decreasing the burst effect of protein from PLGA microspheres", J. Pharm Sci; 92:1582-91, (2003).
Gage, F. "Mammalian neural stem cells." Science 287(5457): 1433-8, (2000).
Goetz et al. "A Highly Conserved Amino-terminal Region of Sonic Hedgehog is Required for the Formation of its Freely Diffusible Multimeric Form" J.Biol Chem, Feb. 17, 281(7):4087-4093, (2006).
Guerrero I, Chiang C., "A conserved mechanism of Hedgehog gradient formation by lipid modifications." Trends Cell Biol. Jan;17(1):1-5, (2007).
Harel, N. Y. And S. M. Strittmatter, "Can regenerating axons recapitulate developmental guidance during recovery from spinal cord injury?" Nat Rev Neurosci 7(8) pp. 603-616 (2006).
Jessell,1. M. (2000). "Neuronal specification in the spinal cord: inductive signals andtranscriptional codes." Nat Rev Genet vol. 1, pp. 20-29 (2000).
Jiang C, Moore MJ, Zhang X, Klassen H, Langer R, Young M "Intravitreal injections of GDNF-loaded biodegradable microspheres are neuroprotective in a rat model of glaucoma" Mol Vis. Sep. 24;13:1783-92 (2007).
Johnson and R. L Tabin, C "The Long and Short of hedgehog signaling" Cell vol. 81,313-316 (1995).
Karlin and Altschul, "Application and statistics for multiple high-scoing segments in molecular sequences", Proc. Natl. Acad. Sci. USA (1993), vol. 90 pp. 5873-5877.
Karlin and Altschul, "Methods for assessing the statistical significance of molecular sequence features by using general scoring schemes" Proc. Natl. Acad. Sci. USA 87:2264, (1990).
Kim B, Dai HN, McAtee M, Bregman BS. "Modulation of dendritic spine modeling in the motor cortex following spinal cord injury: effects of environmental enrichment and combinatorial treatment with transplants and neurotrophin-3" J. Comp Neurol, 508 pp. 473-486 (2008).
Lai et al.,"Patterning of the neural ectoderm of xenopus laevis by the amino-terminal product of hedgehog autoproteoly1ic cleavage" Development 121 :2349-2360 (1995).
Li, S., et al. , "Transgenic inhibition of Nogo-66 receptor function allows axonal sprouting and improved locomotion after spinal inJury" Mol Cell Neurosci 29(1): 26-39 (2005).
Lopez-Martinez et al., "Limb-patterning activity and restricted posterior localization of the amino-terminal product of Sonic hedgehog cleavage", Curr. BiOI5:791-796(1995).
Lowry, N. A. and S. Temple "Making human neurons from stem cells after spinal cord injury." PLoS Med vol. 44, pp. 236-238, (2007).
Lowry, N., et al.,. "Multipotent embryonic spinal cord stem cells expanded by endothelial factors and Shh/RApromote functional recovery after spinal cord injury" Exp Neurol. vol. 290, pp. 510-522 (2007).
Lu et al., "Sonic Hedgehog-Regulated Oligodendrocy1e Lineage Genes Encoding bHLH Proteins in the Mammalian Central Nervous System", vol. 25, pp. 317-329 (2000).
Lu et al., "Common Developmental Requirement for Olig Function Indicates a Motor Neuron/Oligodendrocy1e Connection" Cell, vol. 109, pp. 75-86 (2002).
Lu P, Tuszynski MH, "Growth factors and combinatorial therapies for CNSregeneration." Exp Neurol. vol. 209(2) pp. 313-320, (2008).
Anderberg L, Aldskogius H., Holtz A. "Spinal cord injury—scientific challenges for the unknown future", Ups J Med Sci. (2007); 112(3):259-88.

(56) References Cited

OTHER PUBLICATIONS

Ya-Ping et al., "PEGylated PLGA nanoparticles as protein carriers: Synthesis, preparation, and biodistribution in rats", J. of Controlled Release, 71, (2001), pp. 203-211.
Mu et al. Taxol, "PLGA nanoparticles containing vitamin E TPGS", J. of Controlled release, 86 (2003), 33-48.
Govender et al., "PLGA nanoparticles prepared by nanoprecipitation: drug loading and release studies of a water soluble drug", J. of Controlled Release 57,1999, pp. 171-185.
Dominguez et al., (1996) Science 272, 1621-1625.
Von Burkersroda et al. Biomaterials (2002), 23:4221-4231.
Sara J. Taylor et al., Controlled Release of Neurotrophin-3 from Fibrin Gels for Spinal Cord Injury, 98 J. Control. Release 281-294 (2004).
Sara J. Taylor & Shelly E. Sakiyama-Elbert, Effect of Controlled Delivery of Neurotrophin-3 from Fibrin on Spinal Cord Injury in a Long Term Model, 116(2) J. Control. Release 204-210 (Nov. 28, 2006).
Lu et al., The Journal of Neurosc, vol. 24: pp. 6402-6409, 2004.

* cited by examiner

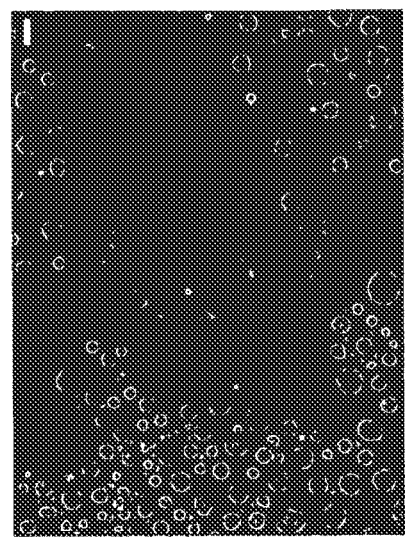
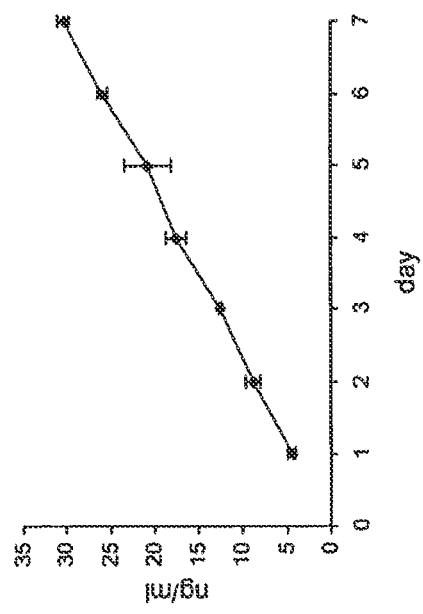
Figure 1A
Figure 1B

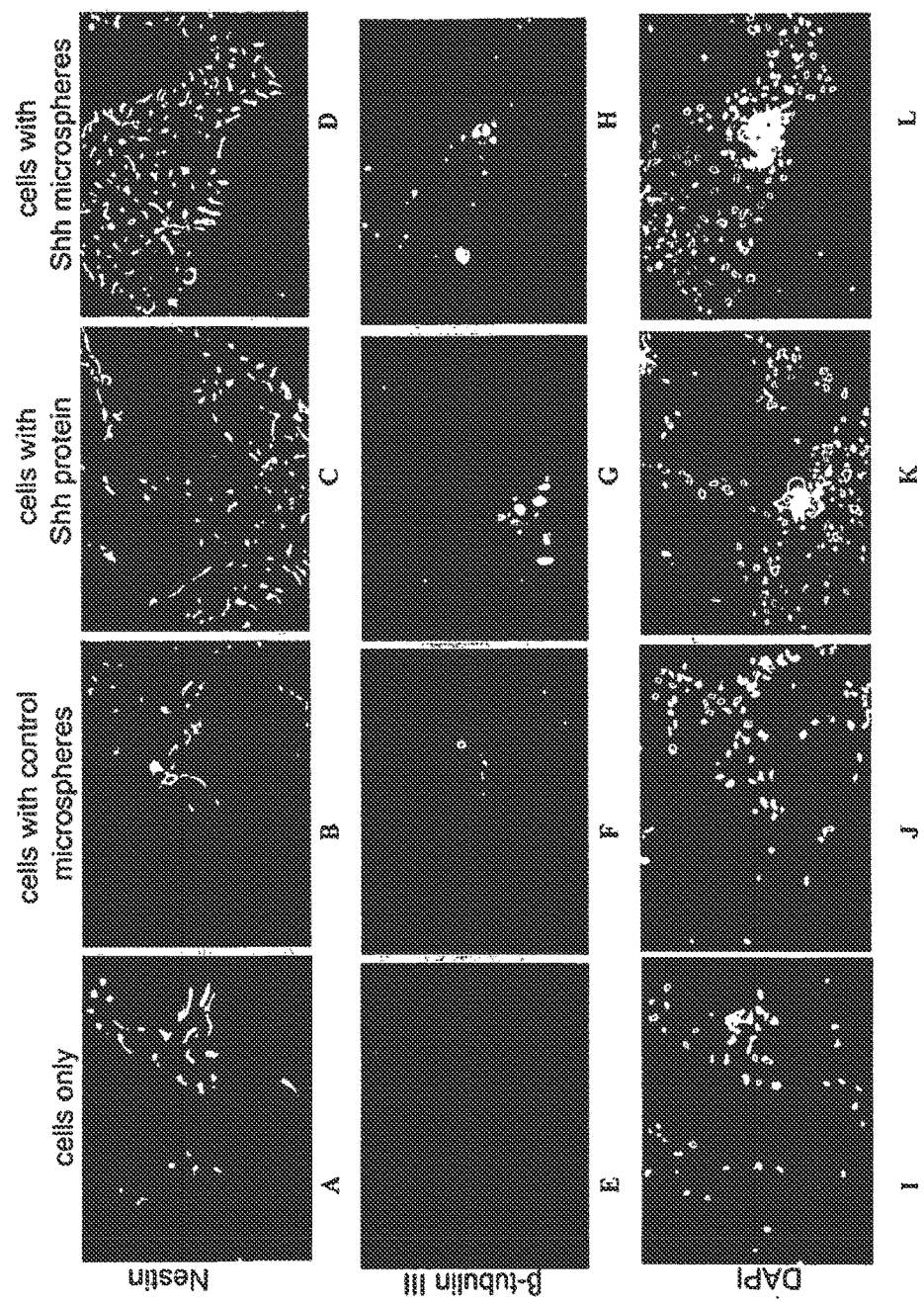
Figure 2A-L

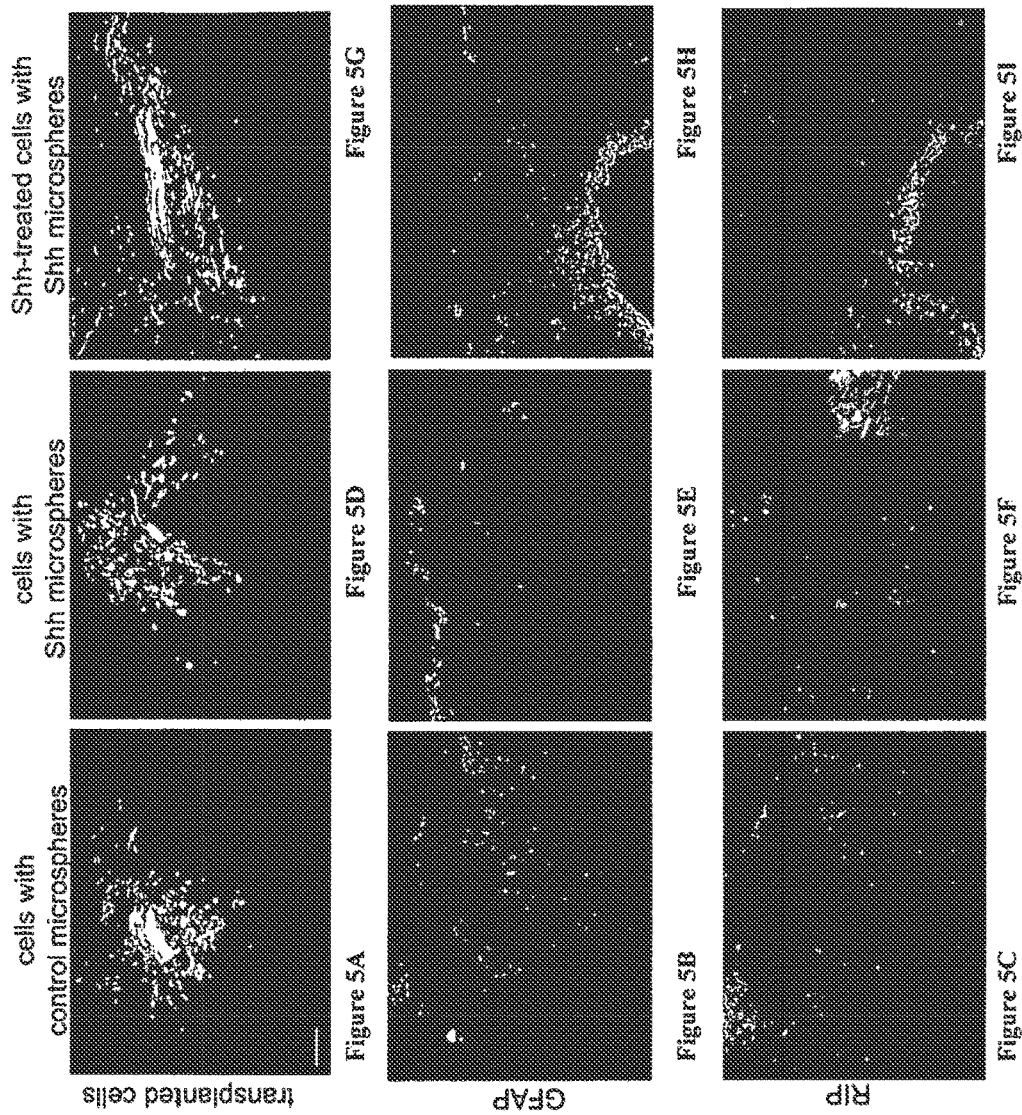

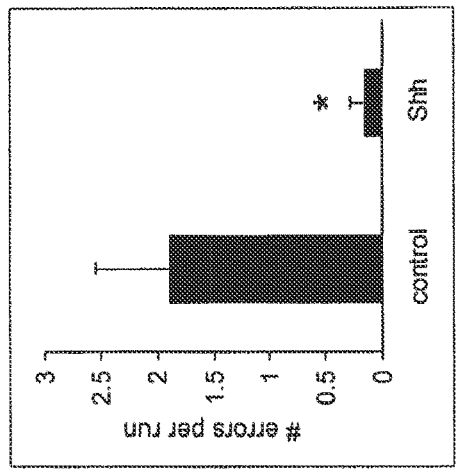
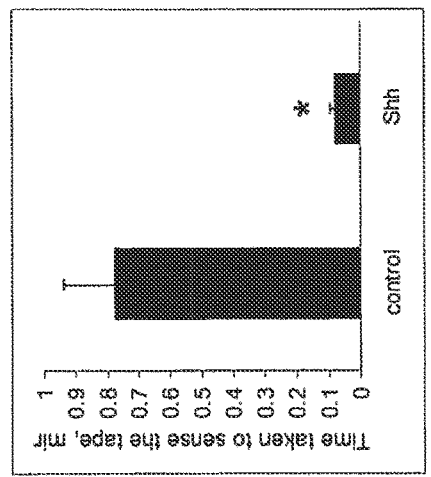
Figure 7A
Figure 7B
Figure 7C

US 10,369,192 B2

METHODS AND COMPOSITIONS FOR DELIVERY OF EXOGENOUS FACTORS TO NERVOUS SYSTEM SITES

CROSS REFERENCE TO RELATED APPLICATIONS

The present application is a continuation of U.S. patent application Ser. No. 13/108,552 filed May 16, 2011, which is a continuation of U.S. patent application Ser. No. 12/398,888 filed Mar. 5, 2009, which claims priority under 35 U.S.C. § 119 to U.S. Provisional Application Ser. No. 61/034,068, filed Mar. 5, 2008. The contents of these prior applications are hereby incorporated by reference in their entireties.

GOVERNMENT SPONSORED RESEARCH OR DEVELOPMENT

This invention was made in pan in the course of research sponsored by the New York State Spinal Cord Injury Research Trust Fund through New York State Department of Health Contract # C020922. New York State may have certain rights in this invention.

REFERENCE TO SEQUENCE LISTING

The specification includes a Sequence Listing, which was submitted to the United States Patent and Trademark Office on Nov. 12, 2013 as an ASCII compliant text file, 362,539 bytes in size, which was created on Nov. 12, 2013 and named "SEOLST.TXT." The contents of the aforementioned Sequence Listing are hereby incorporated by reference and in their entirety.

FIELD OF THE INVENTION

The present invention relates to treatments and methods for sustained delivery of one or more exogenous factors to predetermined sites in the mammalian nervous system. In certain embodiments, the invention relates to the use of biodegradable microspheres to deliver exogenous factors, such as the morphogenic factor, sonic hedgehog (Shh), to the site of spinal cord injury. In other embodiments, the Shh-releasing microspheres are administered together with stem cells, which may be spinal cord neural stem cells.

BACKGROUND OF THE INVENTION

Spinal cord injury (SCI) causes loss of spinal cord cells, damage to ascending and descending axonal tracts and loss of myelination, resulting in paralysis. After SCI, axonal regeneration is prevented by the lack of matrix that supports growth through production of important growth and morphogenic factors (Harel and Strittmatter 2006; Lu and Tuszynski 2007). Successful treatment of SCI will include approaches that aid in the regeneration of damaged axons and/or in the replacement of oligodendrocytes to improve myelination.

Stem cell therapy has been envisioned as a treatment that may serve to prevent and/or reverse SCI by replacing damaged or lost spinal cord cells, delivering factors conducive to spinal cord repair, and providing a physical scaffold for instructing and enabling axon regrowth. However, at present, the technology to successfully direct stem cell differentiation into the appropriate or desired cell type in vivo is lacking. Specifically, research studying stem cells in the context of treating SCI has shown that transplanted neural stem cells (NSC) do not differentiate into the appropriate cell types for neuron regeneration, such as oligodendrocytes and neurons. NSCs instead differentiate into primarily astrocytes in vivo, thereby limiting functional recovery (Enzmann et al. 2006).

One reason functional recovery from SCI is limited is because the microenvironment of the adult spinal cord lacks the necessary biological cues for proper differentiation of NSCs into neurons and oligodendrocytes. The spinal cord microenvironment instead favors astrogliogenesis, (the growth of astrocytes), thereby adding to the astroglial scar, which is believed to be an impermeable barrier to recovering, outgrowing axons (Silver and Miller 2004). It has been demonstrated in vitro that exogenous factors are needed to direct NSC differentiation toward the cell types useful for SCI treatment, including oligodendrocytes and neurons (Cattaneo 1990; Gage 2000).

Achieving delivery of soluble growth factors to the site of SCI is a challenging problem. If injected once, soluble factors flow away quickly from the injury site after injection. Furthermore, long-term pumps, which have been used in other applications to deliver soluble factors, are difficult to use in SCI patients, as the human spinal cord moves significantly as a result of respiratory variations and the pulse, thus catheters tend to migrate. A need exists for a method that can provide sustained delivery of important growth factors to the site of injury over a prolonged period of time.

Sonic hedgehog (Shh) is a multifunctional factor that acts as a morphogen early in spinal cord development, when different cell types are established (Jessell 2000), and as a guidance factor for the commissural axons at later developmental stages (Charron et al. 2003). Specifically, Shh influences the glial choice by inducing oligodendrocyte differentiation and inhibiting the astrocyte lineage (Tekki-Kessaris et al. 2001; Sussman et al. 2002; Agius et al. 2004); Shh treatment in vitro results in the enhancement of neurite outgrowth from dorsal root ganglion neurons (So et al. 2006). Direct injection of soluble Shh into the spinal cord at the time of injury results in improved nerve-to-muscle conductivity, although no functional recovery is observed. Functional recovery can be measured in terms of improved motor or sensory function, usually assessed with behavioral tests, such as measuring the ability of mice to walk on a horizontal ladder. The failure to improve function is likely due to rapid clearance of Shh from the central nervous system (CNS) (Bambakidis and Miller 2004).

Spinal cord injuries are not only common, but they are at present difficult to treat, because NSCs do not differentiate on their own into oligodendrocytes and neurons. While some growth factors, such as Shh, are known to drive this differentiation, it has up to now not been known how to harness this beneficial effect in vivo. Thus, there is a longstanding unfulfilled need for effective spinal cord injury treatments, and also, more generally, for treatments useful in the CNS that would provide or result in the delivery of an effective amount of a desired exogenous factor to the spinal cord or nervous system location to facilitate neural cell recovery (e.g. to provide a niche for growth and repair in this environment).

SUMMARY OF THE INVENTION

The present invention provides methods for treating spinal cord injury in a patient in need of such treatment, by administering to the site of spinal cord injury a sustained delivery composition that includes one or more exogenous factors. In other embodiments, the method is useful for treating a nervous system injury or for increasing neural cell growth in a desired target location.

In yet another embodiment, the invention relates to a method for delivering one or more exogenous factors to a neural cell or nervous system site by administering an effective amount of a sustained delivery composition comprising one or more exogenous factors and, optionally, an effective amount of stem cells to the neural cell or nervous system site.

In yet another embodiment, the invention relates to a method for treating a nervous system injury in a mammal by administering to a mammal in need of such treatment an effective amount for treating the nervous system injury of a pharmaceutical formulation containing at least one exogenous factor, said pharmaceutical formulation providing sustained delivery of the at least one exogenous factor for at least about 7 days.

In yet another embodiment, the invention relates to a method for increasing neural cell growth or regenerating neural cells in a mammal by administering to a mammal in need of such treatment an effective amount for increasing neural cell growth or regenerating neuronal cells of a sustained release pharmaceutical formulation containing at least one exogenous factor, said pharmaceutical formulation continuously delivering the at least one exogenous factor for at least about 7 days.

In certain embodiments, the mammal is a human.

In certain embodiments, the nervous system injury is selected from the group consisting of spinal cord injury, amyotrophic lateral sclerosis (ALS), peripheral nerve injury, and spinal nerve injury.

In yet another embodiment, the sustained delivery composition comprises a plurality of biodegradable microspheres.

In yet another embodiment, the pharmaceutical formulation further contains an effective amount of stem cells, wherein the amount of stem cells in combination with said at least one exogenous factor is effective for treating a nervous system injury.

In yet another embodiment, the at least one exogenous factor is a growth factor selected from the group consisting of Nerve Growth Factor (NGF), Glial Cell Line-Derived Growth Factor (GDNF), Neurotrophin (NT) 3, NT 4/5, NT 6, Ciliary Neurotrophic Factor (CNTF). Leukemia Inhibitory Factor (LIF), Interleukin 6 (IL6), Interleukin 11 (IL11), Cardiotrophin 1, a growth factor hormone, hyaluronidase, chondroitinase ABC (CABC), basic fibroblast growth factor (bFGF), insulin-related growth factor (IGF-I), brain-derived neurotrophic factor (BDNF), epidermal growth factor (EGF), and sonic hedgehog (Shh).

In yet another embodiment, the stem cells are neural stem cells.

In yet another embodiment, the pharmaceutical formulation is administered by at least one injection, wherein a first injection is administered at the site of nervous system injury.

In yet another embodiment, a second injection is administered at a site rostral to the site of nervous system injury.

In yet another embodiment, the stem cells are endothelial-expanded stem cells.

In yet another embodiment, the endothelial-expanded stem cells are pre-treated with sonic hedgehog.

In yet another embodiment, the endothelial-expanded stem cells are pre-treated with sonic hedgehog and retinoic acid.

In yet another embodiment, the invention relates to a pharmaceutical formulation containing an effective amount for increasing neuronal cell growth or regenerating neuronal cells of at least one sustained delivery composition containing at least one exogenous factor selected from the group consisting of Nerve Growth Factor (NGF), Glial Cell Line-Derived Growth Factor (GDNF), Neurotrophin (NT) 3, NT 4/5, NT 6, Ciliary Neurotrophic Factor (CNTF), Leukemia Inhibitory Factor (LIF), Interleukin 6 (IL6), Interleukin 11 (IL11), Cardiotrophin 1, a growth factor hormone, hyaluronidase, chondroitinase ABC (CABC), basic fibroblast growth factor (bFGF), insulin-related growth factor (IGF-I), brain-derived neurotrophic factor (BDNF), epidermal growth factor (EGF), and sonic hedgehog (Shh), wherein the composition provides sustained delivery of at least one exogenous factor for at least 7 days, and a pharmaceutically acceptable excipient.

In certain embodiments, the effective amount of stem cells, wherein the amount in combination with the at least one exogenous factor is effective for increasing neural cell growth or regenerating neural cells.

In certain embodiments, the at least one sustained delivery composition contains a plurality of biodegradable microspheres.

In yet another embodiment, the stem cell is a neural stem cell. In yet another embodiment, the stem cell is an endothelial-expanded stem cell. In yet another embodiment, the endothelial-expanded stem cell is pre-treated with sonic hedgehog. In yet another embodiment, the endothelial-expanded stem cell is pre-treated with sonic hedgehog and retinoic acid.

In yet another embodiment, the sustained delivery composition releases from about 1 ng/ml to about 20 ng/ml Shh for at least 7 days. In certain embodiments, the sustained delivery of one or more exogenous factors is preferably about at least 7 days, and more preferably, about at least 2 weeks.

In certain embodiments, the exogenous factor or factors are growth factors or morphogenic factors. In one embodiment. Shh is the exogenous factor.

In a still further embodiment, the invention provides a pharmaceutical composition containing a biodegradable microsphere loaded with sonic hedgehog (Shh) or an active Shh fragment in which the biodegradable microsphere provides sustained release of Shh for at least about 7 days, and more preferably, at least about 2 weeks. In certain embodiments, the pharmaceutical composition further comprises neural stem cells.

BRIEF DESCRIPTION OF THE DRAWINGS

FIGS. 1A-B show effects of Shh release. FIG. 1A demonstrates the continuous release of Shh by microsphere compositions over time in vitro. FIG. 1B demonstrates that microspheres co-cultured with spinal cord NSCs are not toxic to the NSCs.

FIGS. 2A-L illustrate that direct treatment with Shh and treatment with Shh-releasing microspheres induces increased proliferation and neurogenesis of spinal cord NSCs. E9 spinal cord cells were cultured for 6 days. Shh protein or supernatant from control (PLGA only) or Shh-releasing microspheres was added to the indicated cultures daily. Cultures were stained for nestin (progenitor cells), β-tubulin III (neurons) and DAPI (nuclei).

FIGS. 5A-I demonstrate that transplanted NSCs graft successfully in the spinal cord in all experimental groups.

FIGS. 7A-C show motor recovery after transplantation of Shh/RA-BPAE-expanded NSCs into spinal cords of mice in a murine model of SCI.

DETAILED DESCRIPTION

Figure 3B:
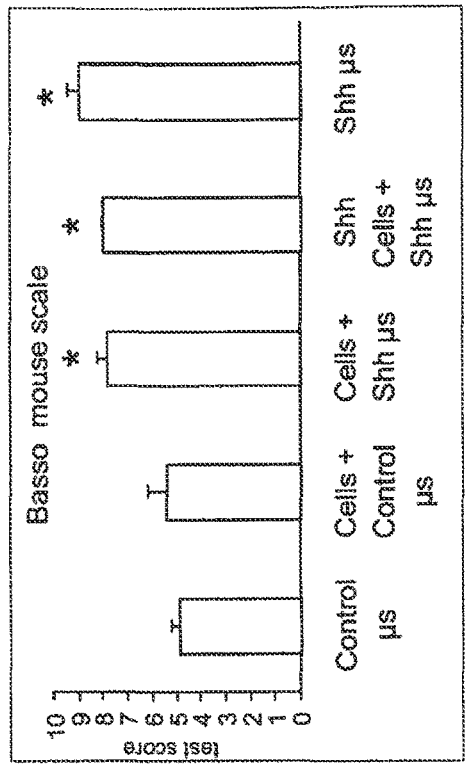
FIGS. 3A-D illustrate motor recovery in mice with SCI following treatment with Shh-containing microspheres with or without Shh-treated spinal cord neural stem cells.

Spinal cord injury (SCI) in mammals causes loss of spinal cord cells, damage to ascending and descending axonal tracts and loss of myelination, resulting in paralysis. After SCI, axonal regeneration is prevented by the lack of matrix that supports growth through production of important growth and morphogenic factors (Harel and Strittmatter 2006; Lu and Tuszynski 2007). Successful treatment of SCI will include approaches that aid in the regeneration of damaged axons.

Regeneration of damaged axons encompasses several types of neuronal response to injury; direct regrowth of severed axons represents 'true' axonal regeneration, whereas sprouting from nearby uninjured fibers or proximal locations along severed axons has a compensatory role. Adult nerve fibers often display haphazard growth and are unable to efficiently reform functional circuits. To maximize the effectiveness of repair of the damaged spinal cord, a more faithful recapitulation of developmental pathfinding and circuit refining mechanisms would be beneficial. At least two approaches to recapitulating development in the injured CNS may be employed: (1) re-establishing crucial developmental cues in the correct pattern to guide regenerating axons, and (2) maximizing the sprouting and plasticity of intact fibers through sensory feedback rehabilitation techniques. See, Harrel and Strittmatter, (2006).

For neuronal differentiation and migration, a set of diffusible signaling molecules directs the differentiation of ectodermal tissue into discrete regions along the early neural tube. Molecules that inhibit bone morphogenetic protein 4 signaling nudge ectodermal tissue down the neural pathway. Basic fibroblast growth factors (bFGFs) and WNT proteins stimulate differentiation into anterior neural structures, whereas retinoids stimulate posterior neural fates. In the developing spinal cord, the floor plate and nearby notochord secrete sonic hedgehog (Shh), which signals the ventral cord to differentiate into motor neurons and ventral inter neurons. Many of these morphogens (such as growth factors) have been shown to also function as axon guidance molecules. In addition, several morphogens persist after development, when they might continue to regulate stem cell division and differentiation. The role of adulthood morphogens in the context of CNS injury is not well characterized. Id.

Whereas cell-autonomous mechanisms contribute to limiting adult axon growth, extrinsic factors appear to have an even more crucial role in blocking adult CNS regeneration. Classic experiments have demonstrated the more inhibitory nature of the CNS for axon outgrowth. Subsequent experiments have suggested that this inhospitable milieu results primarily from the presence of CNS myelin-specific inhibitory factors rather than a lack of positive factors. Furthermore, the age at which most species lose the ability to regenerate after SCI coincides with spinal cord myelination. However, myelin is not the only extrinsic barrier to adult CNS regeneration. CNS injury induces reactive astrocytes to release many molecules that inhibit regeneration, including chondroitin sulphate proteoglycans (CSPGs), carbohydrate-rich extracellular molecules with inhibitory effects on neurite outgrowth produced predominantly by astrocytes, and other glial scar components. Furthermore, breakdown of the blood-brain barrier results in the recruitment of inflammatory cells and cytokines that have a more complicated effect on CNS regeneration. Interestingly, as with many axon guidance molecules, several myelin-associated inhibitors (MAIs) and CSPGs are expressed during development as well as in the adult. For example, Nogo isoforms are expressed by both central and peripheral neurons at developmental stages before the onset of oligodendrocyte Nogo expression. Id.

Depending on the type of CNS injury, attempts at regeneration might need to recapitulate all or only some of the stages of development described above. For example, full regeneration after stroke or neurodegenerative disease would require the replacement of lost neurons, followed by the regeneration and guidance of projections over the entire distance covered by the absent tracts. By contrast, recovery from SCI could occur through encouraging sprouting and guidance from spared tracts, as well as maximizing plasticity of spared and regenerated circuits. The present invention provides methods for achieving recovery from CNS injury, for example, by stimulating neuron sprouting, regrowth, development and/or circuit plasticity in the adult CNS.

Stimulating neuronal cell growth/preventing neuronal cell degeneration, can be beneficial for other conditions that affect the central spinal cord and the spinal nerves. For example, in ALS motor neurons die, and it has been shown that delivery of growth factors such as VEGF can be beneficial to prevent loss of these cells in a mouse model (Storkebaum, 2005). Motor neurons project out to the periphery and there is evidence that damage to peripheral nerves can involve Shh in repair processes. For example, in sciatic nerve injury, a common condition, it has been shown recently that shh is upregulated in schwann cells adjacent to crush-injured sciatic nerve, and that this is followed by an increase in brain-derived neurotrophic factor (BDNF) expression. They found that administration of cyclopamine, a hedgehog inhibitor, to the injured site prevented the increase in BDNF expression and deteriorated motor neuron survival after sciatic nerve injury. When peripheral Schwann cells were treated with exogenous Shh, BDNF was increased suggesting that adding Shh could help promote a beneficial repair environment (Hashimoto, 2008). In a different study more substantial peripheral nerve injuries were found to elicit extensive axon sprouting that was coincident with an increase in shh mRNA, raising the possibility that an exogenous supply of Shh can help promote peripheral nerve sprouting after injury (Xu, Zochodne 2008). Based on the results described below, it is expected that addition of Shh via microbeads into sciatic nerve will augment the repair process.

Certain aspects of the present invention encompass the therapeutic application of an Shh-containing microsphere to increase or enhance survival and outgrowth of neurons and other neuronal cells in the central nervous system. The ability of Shh to regulate neuronal differentiation during development of the nervous system and also presumably in the adult state indicates that Shh can be reasonably expected to facilitate control of adult neurons and other nervous system cells. This includes but is not limited to the maintenance, functional performance, and aging of normal cells, the repair and regeneration processes in chemically or mechanically lesioned cells, and the prevention of degeneration and premature death resulting from loss of differentiation in certain pathological conditions.

In light of this understanding, the present invention specifically contemplates applications of the subject method to the treatment of (prevention and/or reduction of the severity of) neurological conditions deriving from: acute, (e.g., SCI), subacute, or chronic injury to the nervous system, including traumatic injury, chemical injury, basal injury and deficits (such as the ischemia resulting from stroke). In acute injury, cells including neurons, astrocytes and oligodendrocytes die and there is an inflammatory reaction. With time, a fluid-filled cyst can appear that forms a barrier to axon growth. With time, damaged axons can die back and further degeneration of neurons and of the associated glial cells, such as the myelinating cells occurs. In addition, a scar consisting of astrocytes and chondroitin sulfact proteoglycans can build up, both of which are inhibitory to new axon growth. In a chronic situation then, there may be irreversible loss of spinal cord cells, and the creation of barriers, so that repair will be more involved and require more cells and regrowth than in the acute injury situation. (Anderberg L, Aldskogius H, Holtz A. Spinal cord injury—scientific challenges for the unknown future. Ups J Med Sci. 2007; 112(3):259-88.)

In an illustrative embodiment, the subject method is used to treat amyotrophic lateral sclerosis (ALS), a disease of the nerve cells in the brain and spinal cord that control voluntary muscle movement. In ALS, neuronal cells waste away or die, and can no longer send messages to muscles. This eventually leads to muscle weakening, twitching, and an inability to move the arms, legs, and body. The condition slowly gets worse. When the muscles in the chest area stop working, it becomes hard or impossible to breathe on one's own. ALS affects approximately 1 out of every 100,000 people. ALS patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of Shh-containing microspheres with or without NSCs in the spinal cord may reverse motor neuron degeneration in ALS patients.

In yet additional embodiments, microspheres of different types or sizes, or the same microspheres containing different exogenous factors or different combinations of exogenous factors are mixed, allowing for a combinatorial treatment regime, which is another desirable treatment option for SCI treatment. For example, microspheres carrying scar-digesting enzymes are mixed with microspheres carrying growth factors. In an additional embodiment, microspheres are used to create an artificial environment or niche to instruct stem cell differentiation, such as would be useful after implantation of spinal cord NSCs into the site of SCI. Non-limiting examples of methods using combinational therapy are described in detail in Lu et al. (2008) and Ashton et al. (2007).

In certain aspects the present invention encompasses methods for the stimulation of endogenous neural stem cells (NSC). In some aspects the methods involve time-release mechanisms for the release of morphogenic factors, such as, e.g., Shh, to neural sites. Non-limiting examples of time-release mechanisms include microspheres, which, herein, may also be referred to as 'beads' or "microbeads," alginate gels, and nanoparticles. [See, e.g., Ashton, et al. (2007) Biomaterials. 28, 36, 5518; Drury, J. L. et al. (2003) Biomaterials; 24:4337-4351; U.S. Pat. No. 7,226,617 to Ding et al.; Simmons, C. A. et al. (2004) Bone; 35:562-569 As used herein. "nanoparticles" are often defined as small particles that are sized in the range of 1-100 nanometers (nm), but also include sub-micron as well as larger particles encompassing the range of 1-1000 nm. See, for example: Ya-Ping Li, et al., PEGylated PLGA nanoparticles as protein carriers: Synthesis, preparation, and biodistribution in rats. J. of Controlled Release, 71, 2001, pages 203-211; A novel controlled release formulation for the anticancer drug paclitaxel (Taxol): PLGA nanoparticles containing vitamin E TPGS. J. of Controlled release, 86, 2003, 33-48; and Govender et al. PLGA nanoparticles prepared by nanoprecipitation: drug loading and release studies of a water soluble drug. J. of Controlled Release 57, 1999, pages 171-185.

A time release schedule can be achieved by a series of scheduled multiple injections. In one aspect of the present invention, a niche that maintains NSC in an active state is reconstructed or mimicked, for example, for a specific length of time. Doing so facilitates the control of the number of cells created from endogenous NSC and in some examples, the type of progeny (i.e., cell type) that can be derived from or produced by the activated NSC. Activated NSC is the NSC that is actively proliferating and generating progeny.

Contemplated in the present invention are methods for the treatment of diseases or injuries to nervous system sites including spinal cord, peripheral nervous system, and spinal nerve injuries. These include the following, non-limiting examples.

I) Spinal Cord Injury:
Shh loaded microspheres according to the present invention can be used to stimulate endogenous NSC to repair spinal cord injury. As described below, a mouse model for spinal cord injury is applicable to humans and also to other nerve injuries, as set forth in Examples II-IV, below. Other diseases of the spinal cord, such as ALS and spinal cord tumors may also be treated according to methods of the present invention. The present invention also provides methods for inducing the maintenance, growth, or regeneration of neuronal cells, such as, e.g., motor neurons.

II) Peripheral Nerve Injury:
Peripheral nerve injury, such as seen in sciatica and other peripheral neuropathies, can be treated according to the methods of the present invention. Microspheres according to the embodiments of the present invention are injected into the area of damage to this nerve. Shh increases after peripheral nerve injury and that this is important for the repair process, based for example on evidence that inhibition of hedgehog signaling is inhibitory to peripheral repair, while addition of shh increases beneficial growth factors such as BDNF. There are a number of different hedgehogs described to date-sonic, desert and Indian for example, but they all converge on a similar signaling system and are all inhibited by cyclopamine. Thus, compositions and methods of the present invention, namely injection of sustained release Shh microspheres or other suitable compositions are expected to provide improvements for peripheral nerve injury. In some embodiments, sustained release Shh compositions may be held in place by putting them in alginate gels, which together with the beads will eventually dissolve.

The present methods encompass in part a technique for transplantation or administration of endothelial-expanded spinal cord stem cells that were treated with Shh and retinoic acid to the site of a spinal cord injury. The results show that the methods of the present invention result in functional recovery from SCI as exemplified by the studies in mouse models described in detail below. It is determined that treatment according to methods of the present invention results in motor recovery when at least about 80% of motility is regained, following SCI. Further, it is determined that treatment according to the methods of the present invention results in sensory recovery when at least about 80% of sensory ability is regained, such as determined by the tape removal assay. Further, recovery is determined to be achieved if the increase in motor or sensory function is statistically significant compared to the negative control (e.g. mock-treated mice having SCI).

In certain embodiments, the present invention relates to a method for sustained delivery of one or more exogenous factors, such as Shh, in vivo using biodegradable microspheres engineered to slowly release the desired factor(s) over about at least a seven-day period. The data show that delivery of biodegradable microspheres releasing Shh administered alone, as well as administration of a combination of Shh-releasing microspheres and endothelial-expanded Shh-treated spinal cord NSCs, provide beneficial results in a murine, dorsal column model of SCI.

In additional embodiments, methods described herein for treatment of neural cell damage, inducing neural cell regrowth, and for inhibiting astrogliogenesis, are applied to mammals, and preferably to humans. Mouse models of SCI closely mimic characteristics of human SCI and provide a useful tool for understanding human SCI, as well as related neural injuries.

After spinal cord injury, loss of spinal cord cells and damage of sensory and motor tracts leads to paralysis. While it is thought that the use of stem cells may present a viable treatment, the natural microenvironment of the spinal cord does not facilitate differentiation of NSCs into appropriate neural cell types. Certain growth factors, such as Shh, must be present for a sustained period of time, of about at least one week, in order for correct differentiation to occur. The inventors have developed a method that allows delivery of biologically active factors to the site of the injury by incorporation of these factors into biodegradable microspheres. This creates a minimally invasive method for prolonged growth factor delivery.

Shh regulates various aspects of embryonic development both in vertebrates and invertebrates (for reviews see Perrimon, N. (1995) Cell 80, 517-520 and Johnson, R. L, and Tabin, C (1995) Cell 81, 313-316). It is involved in anterior-posterior patterning, formation of an apical ectodermal ridge, hindgut mesoderm, spinal column, distal limb, rib development, and lung development, and inducing ventral cell types in the spinal cord, hindbrain and forebrain.

While the mechanism of action of Shh is not fully understood, the most recent biochemical and genetic data suggest that the receptor for Shh is the product of the tumor suppressor gene, patched (Marigo, V., et al. (1996) Nature 384, 176-179; Stone, D. M., et al. (1996) Nature 384, 129-134) and that other proteins; smoothened (Stone, D. M., et al. (1996) Nature 384, 129-134; Alcedo, J., et al. (1996) Cell 86, 221-232), Cubitus interruptus (Dominguez, M., et al. (1996) Science 272, 1621-1625; Alexandre, C., et al. (1996) Genes & Dev. 10, 2003-2013), and fused (Therond, P. P., et al. (1996) Proc. Natl. Acad. Sci. USA 93, 4224-4228) are involved in the Shh signaling pathway.

The full-length human Shh protein has been described and has protein accession number NP_000184 (SEQ ID NO:1). The mouse Shh protein has also been described and has protein accession number CAA53922 (SEQ ID NO:3). Coding sequences for Shh include accession numbers AC_000068 (human, SEQ ID NO:6) and X76290 (murine, SEQ ID NO:7). Additional mammalian Shh proteins, such as SEQ ID NO:4, SEQ ID NO:5, and those described in U.S. Pat. Nos. 6,664,075; 6,271,363; 6,165,747. Any full-length Shh proteins, or Shh active fragments are useful in the present invention. Additionally, in the presently described experiments, human Shh amino terminal active fragment was utilized, but similar experiments using mouse Shh showed that the active fragments both functioned in a similar manner. It is contemplated that human Shh and active fragments of the protein will be used for pharmaceutical formulations to be administered in humans.

Shh is produced as a 47-49 kDa-secreted (depending on species) protein that post-translationally cleaves to give two mature proteins: an approximately 19-kDa amino-terminal fragment that remains cell associated and a 29-31-kDa carboxy terminal fragment that is released from the cell. The membrane-associated amino-terminal fragment contains the signaling portion of the molecule. The mouse Shh (mShh) precursor carboxy terminus encodes the autoprocessing domain which acts only in cis. The N-terminal peptide is both necessary and sufficient for short- and long-range Shh signaling activities, and therefore, fragments of Shh are also biologically active and important (Porter, J. A. et al. (1995) Nature 374:363: Lai et al. (1995) Development 121:2349-2360; Roelink, H. et al. (1995) Cell 81:445-455: Porter, J. A. et al. (1996) Science 274:255; Fietz, M. J. et al. (1995) Drosophila. Curr. Biol. 6:643-650; Fan, C. M. et al. (1995) Cell 81:457-465; Mart, E., et al. (1995) Nature 375:322-325; Lopez-Martinez et al. (1995) Curr. Biol 5:791-795; Ekker, S. C. et al. (1995) Development 121:2337-2347; Forbes, A. J. et al. (1996) Development 122:112; Goetz et al. (2006) J. Biol. Chem. February 17; 281(7):4087-93). Furthermore, Shh may be modified post-translationally while maintaining its functional activity. For example, certain hydrophobic modifications of Shh, such as the addition of a long-chain fatty acid at the N-terminus and cholesterol at the C-terminus, greatly activate Shh (Taylor et al. (2001). Biochemistry. April 10; 40(14):4359-71). Any such modified Shh proteins, while exhibiting functional activity are useful in the present invention.

In certain embodiments, the Shh protein comprises SEQ ID NO:1. The Shh protein may also comprise a fragment of SEQ ID NO: 1, wherein the fragment may be any N-terminal or other active fragment of Shh. In other embodiments, the Shh N-terminal fragment comprises SEQ ID NO: 2. In yet further embodiments, the Shh protein comprises SEQ ID NO:3, SEQ ID NO:4, or SEQ ID NO:5.

In yet another embodiment, the Shh protein is encoded by any one of the nucleic acid sequences selected from the group consisting of SEQ ID NO: 6, SEQ ID NO:7, and SEQ ID NO:8.

In certain embodiments, the Shh protein can comprise a full length protein, such as represented in the sequence listings, or it can comprise a fragment of, for instance, at least 5, 10, 20, 50, 100, 150, 200, 250, or 300 amino acids in length. Preferred hedgehog polypeptides include Shh sequences corresponding approximately to the natural proteolytic fragments of the hedgehog proteins, such as from about Cys-24 through about the region that contains the proteolytic processing site, e.g., Ala-194 to Gly-203, or from about Cys-198 through Ala-475 of the human Shh protein, or analogous fragments thereto.

In certain embodiments, Shh protein may be a protein with an N-terminal cysteine that is appended with at least one hydrophobic moiety, a protein with an N-terminal amino-acid that is not a cysteine appended with at least one hydrophobic moiety, or a protein with at least one hydrophobic moiety substituted for the N-terminal amino acid; wherein the protein binds to patched and has at least 80% amino acid identity, or at least 90%-95% identity to a hedgehog amino acid sequence comprising SEQ ID NO: 1, SEQ ID NO:2, SEQ ID NO:3, SEQ ID NO:4, or SEQ ID NO:5. In certain embodiments, the Shh protein may comprise any of the sequences identified by the accession numbers NT_07956.2, AC_000050.1, or NW_923796.1. In certain embodiments, the active agent in the sustained release composition may include a molecule with "Shh-like" activity (e.g., the Curls agonist: Wichterle H, Lieberam I, Porter J A, Jessell T M. Directed differentiation of embryonic stem cells into motor neurons. Cell. 2002 Aug. 9; 110(3):385-97.)

The interaction of Shh with one of its cognate receptors, patched (ptc), sets in motion a cascade involving the activation and inhibition of downstream effectors, the ultimate consequence of which is, in some instances, a detectable change in the transcription or translation of a gene. Shh and its cognate receptor patched (ptc) are expressed in the epithelial and/or mesenchymal cell components of the skin (i.e., the hair follicle). See Parisi et al., (1998) Cell Res 8, 15-21; St. Jacques et al., (1998) Current Biology, 8, 1058-1068; and Dahmane et al., (1997) Nature, 389, 876-880. The two-way interaction between epithelial and the dermal mesenchymal cells directs the subsequent development of hair follicles. Disrupting this interaction might lead to a modulation of proliferation and/or differentiation events that give rise to hair and/or epithelial tissue structures such as the gut.

Another embodiment of the invention concerns the therapeutic application of Shh or other morphogenic factor-containing microspheres to specifically control the type of cell that differentiates from NSC in vivo. For example, the amount of Shh contained within the microsphere can be adjusted to specifically control and induce differentiation of NSC into floor plate, motor neurons, or oligodendrocytes. For example, in vitro, 7-16 nM Shh induces floor plate differentiation, and 4 nM Shh induces the differentiation of motor neurons. See, Roelink et al, 1995 Cell 81 445-455; Ericson et al, 1997; Cell. 1997 Jul. 11; 90(1): 169-80.

Moreover, in the spinal cord, oligodendrocyte precursors (OLPs) emerge from the ventral ventricular zone in a restricted domain near the floor plate—the ventral motor neuron progenitor (pMN) domain, composed of neural progenitors that express the olig gene bHLH transcription factors, which generate motorneurons (MNs) during early development of the neural tube (Lu et al., 2000, 2002; Takebayashi et al., 2002; Zhou and Anderson, 2002). MNs and oligodendrocytes are not produced simultaneously from these progenitors; specification of these lineages occurs in two successive waves, with MNs produced first OLP specification takes place at a time long after dorsoventral neuronal patterning is completed. OLP specification from ventral neural progenitors is optimal at concentrations of Shh much higher than those reported to induce MNs from neural progenitors (12-25 nM) (Danesin C, Agius E, Escalas N, Ai X, Emerson C, Cochard P, Soula C Ventral neural progenitors switch toward an oligodendroglial fate in response to increased Sonic hedgehog (Shh) activity: involvement of Sulfatase I in modulating Shh signaling in the ventral spinal cord. J Neurosci. 2006 May 10:26(19):5037-48.)

Thus, controlling cell type differentiation based on the concentration of Shh is a useful approach for the treatment of diseases of the nervous system in which specific cell types should be induced to proliferate. For example, Shh creates the floor plate and dopaminergic neurons in the midbrain arise from the floorplate. (See, Ono et al., (2007) Development and Disease, 134:3213-3125).

Yet another aspect of the present invention concerns the therapeutic application of an Shh-containing microsphere to enhance survival and outgrowth of neurons and other neuronal cells in both the central nervous system and the peripheral nervous system. In the course of developing the methods of the present invention, a mouse model of SCI was utilized. In this model, SCI was produced in adult mice by performing an operation under anesthetic: the spinal cord was cut halfway through from the back (dorsal) side. At the same time, biodegradable microspheres were injected into the injury site. The microspheres were engineered to release Shh over at least a two week period, at a concentration known to be active in the developing spinal cord. The animals were tested for behavioral motor and sensory skills prior to sacrificing and assessing changes in the cord. The animals receiving the Shh containing microspheres were compared to those that received the microspheres alone (control).

As used herein, the term "behavioral recovery" is understood to include motor (locomotor) and sensory recovery, where motor recovery may be measured, for example, by the horizontal ladder test described herein, and sensory recovery may be measured, e.g., by the tape test discussed in Example 5, below. However, it is understood by those of ordinary skill in the art that the term "behavioral recovery" may also be used interchangeably with the term "motor recovery" (i.e., when only motor, but not sensory, recovery has been assessed).

It was discovered that mice receiving an injection of biodegradable microspheres that release the growth factor Shh into the site of SCI, exhibited motor recovery after injury. This recovery could be explained by the decreased scarring at the site of injury, and by the increased regrowth of a major motor tract—the corticospinal tract. Shh has not previously been shown to stimulate sprouting/increased growth of central nervous system neuronal axon in vivo, hence this is an unexpected action of Shh treatment in vivo.

In one set of experiments, transplantation of Shh-treated stem cells to the injured mouse spinal cord helped improve behavioral outcomes. In another set of experiments, it was found that adding both microspheres releasing Shh and Shh-treated stem cells is even more beneficial than either alone. The release by microspheres of growth factors into the environment around the stem cells can help create a specialized environment or 'niche' to regulate stem cell behavior. This can help drive the stem cells to generate cell fates beneficial for spinal cord injury, such as neurons and oligodendrocytes.

Thus, in a further embodiments, the present compositions and methods will be useful for stimulating endogenous stem cells. Stimulating these endogenous stem cells in the adult spinal cord will provide a therapeutic 'niche' such that damaged neural cells are repaired or replaced, along the lines of Shh function in the embryo.

In a further embodiment, the present compositions and methods will provide benefits for treating individuals with injured or damage to a spinal disc. Such spinal disc damage or injury includes when the disk slips and the nerve roots become contused and/or pinched and damaged. Injection of sustained release Shh compositions or other factors into the nerve root are expected to be beneficial.

In summary, the inventors have developed a method for treating SCI in which microspheres releasing growth factors over a prolonged period are beneficial to the injured site. Specifically, Shh reduces scarring and enhances axon sprouting and outgrowth from the corticospinal tract. Moreover, this method allows a further beneficial effect of adding microspheres plus stem cells, which enhances recovery from SCI and provides a specialized environment around the injured site that is conducive to neuronal cell growth and/or recovery. Thus, in certain embodiments, the compositions and/or methods of the present invention provide a niche for growth and in certain instances expansion of endogenous progenitor/stem cells.

In accordance with the present invention there may be employed conventional molecular biology, microbiology, protein expression and purification, antibody, and recombinant DNA techniques within the skill of the art. Such techniques are explained fully in the literature. See, e.g., Sambrook et at (2001) *Molecular Cloning: A Laboratory Manual.* 3$^{rd}$ ed. Cold Spring Harbor Laboratory Press: Cold Spring Harbor, N.Y.; Ausubel et al. eds. (2005) *Current Protocols in Molecular Biology.* John Wiley and Sons, Inc.: Hoboken, N.J.; Bonifacino et al. eds. (2005) *Current Protocols in Cell Biology.* John Wiley and Sons, Inc.: Hoboken, N.J.; Coligan et al. eds. (2005) *Current Protocols in Immunology*, John Wiley and Sons, Inc.: Hoboken, N.J.; Coico et al. eds. (2005) *Current Protocols in Microbiology*, John Wiley and Sons, Inc.: Hoboken, N.J.; Coligan et al. eds. (2005) *Current Protocols in Protein Science*, John Wiley and Sons, Inc.: Hoboken, N.J.; and Enna et al. eds. (2005) *Current Protocols in Pharmacology*, John Wiley and Sons. Inc.: Hoboken, N.J.; *Nucleic Acid Hybridization*, Hames & Higgins eds. (1985); *Transcription And Translation*, Hames & Higgins, eds. (1984); *Animal Cell Culture* Freshney, ed. (1986); *Immobilized Cells And Enzymes*, IRL Press (1986); Perbal, *A Practical Guide To Molecular Cloning* (1984); and Harlow and Lane. *Antibodies: A Laboratory Manual* (Cold Spring Harbor Laboratory Press: 1988).

The electronic version of the sequence listing containing SEQ ID NOs 1-8 is hereby incorporated by reference in its entirety.

Definitions

The following definitions are provided for clarity and illustrative purposes only, and are not intended to limit the scope of the invention.

As used herein, the term "spinal cord injury (SCI)" in understood to include injury to the spinal cord which causes loss of spinal cord cells, damage to ascending and descending axonal tracts and/or loss of myelination. SCI can result in decreased limb function and/or paralysis. In certain cases, SCI involves acute, subacute or chronic injury to the spinal cord. An example of acute injury includes injury or trauma that occurs less than 12 hours after the injury. An example of subacute injury includes injury or trauma that occurs about 12 hours to about 30 days after injury. An example of chronic injury to the spinal cord includes injury or trauma that occurs over 12 months after spinal cord injury (from the U.S. clinical trials website).

As used herein, the term "stem cell" refers to a cell that retains the ability to renew itself through mitotic cell division and can differentiate into a diverse range of specialized cell types.

As used herein, the term "neural stem cell (NSC)" describes cells that are the self-renewing, multipotent cells that generate phenotypes of the nervous system.

The term "growth factor" can be a naturally occurring, endogenous or exogenous protein, or recombinant protein, capable of stimulating cellular proliferation and/or cellular differentiation.

As used herein, the term "morphogenic factor" refers to a substance governing the pattern of tissue development and, in particular, the positions of the various specialized cell types within a tissue.

As used herein, "neural" means the nervous system and includes glial cells and neurons.

As used herein, "central nervous system" includes brain and/or the spinal cord of a mammal. The term may also include the eye and optic nerve in some instances.

The term "neuron" as used herein describes a nerve cell capable of receiving and conducting electrical impulses from the central nervous system. A nerve cell or "neuron" may typically include a cell body, an axon, axon terminals, and dendrites.

The term "exogenous factor" describes those compounds capable of inducing differentiation of a stem cell into a neuronal cell. These compounds include, but are not limited to antioxidants, trophic factors, morphogenic factors, and growth factors.

As used herein, the term "sustained delivery" includes delivery of an exogenous factor in vive over a period of time following administration, preferably at least a week or several weeks. Sustained delivery of the exogenous factor can be demonstrated by, for example, the continued outgrowth of CNS neurons over time. Alternatively, sustained delivery of the exogenous factor, such as Shh, can be demonstrated by detecting the presence of the exogenous factor in vitro over time.

Expression Construct

By "expression construct" is meant a nucleic acid sequence comprising a target nucleic acid sequence or sequences whose expression is desired, operatively associated with expression control sequence elements which provide for the proper transcription and translation of the target nucleic acid sequence(s) within the chosen host cells. Such sequence elements may include a promoter and a polyadenylation signal. The "expression construct" may further comprise "vector sequences". By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

Expression constructs of the present invention may comprise vector sequences that facilitate the cloning and propagation of the expression constructs. A large number of vectors, including plasmid and fungal vectors, have been described for replication and/or expression in a variety of eukaryotic and prokaryotic host cells. Standard vectors useful in the current invention are well known in the art and include (but are not limited to) plasmids, cosmids, phage vectors, viral vectors, and yeast artificial chromosomes. The vector sequences may contain a replication origin for propagation in *E. coli*; the SV40 origin of replication; an ampicillin, neomycin, or puromycin resistance gene for selection in host cells; and/or genes (e.g., dihydrofolate reductase gene) that amplify the dominant selectable marker plus the gene of interest.

Express and Expression

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself. e.g., the resulting protein; may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "transfection" means the introduction of a foreign nucleic acid into a cell. The term "transformation" means the introduction of a "foreign" (i.e. extrinsic or extracellular) gene, DNA or RNA sequence to a cell, so that the host cell will express the introduced gone or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cells genetic machinery. The gene or sequence may include nonfunctional sequences or sequences with no known function. A host cell that receives and expresses introduced DNA or RNA has been "transformed" and is a "transformant" or a "clone". The DNA or RNA introduced to a host cell can come from any source, including cells of the same genus or species as the host cell, or cells of a different genus or species.

Expression System

The term "expression system" means a host cell and compatible vector under suitable conditions, e.g. for the expression of a protein coded for by foreign DNA carried by the vector and introduced to the host cell.

Gene or Structural Gene

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into an amino acid sequence. Other genes may function as regulators of structural genes or as regulators of DNA transcription.

A coding sequence is "under the control of" or "operatively associated with" expression control sequences in a cell when RNA polymerase transcribes the coding sequence into RNA, particularly mRNA, which is then trans-RNA spliced (if it contains introns) and translated into the protein encoded by the coding sequence.

The term "expression control sequence" refers to a promoter and any enhancer or suppression elements that combine to regulate the transcription of a coding sequence. In a preferred embodiment, the element is an origin of replication.

Heterologous

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. For example, the present invention includes chimeric DNA molecules that comprise a DNA sequence and a heterologous DNA sequence which is not part of the DNA sequence. A heterologous expression regulatory element is such an element that is operatively associated with a different gene than the one it is operatively associated with in nature. In the context of the present invention, a gene encoding a protein of interest is heterologous to the vector DNA in which it is inserted for cloning or expression, and it is heterologous to a host cell containing such a vector, in which it is expressed.

Homologous

The term "homologous" as used in the art commonly refers to the relationship between nucleic acid molecules or proteins that possess a "common evolutionary origin," including nucleic acid molecules or proteins within superfamilies (e.g., the immunoglobulin superfamily) and nucleic acid molecules or proteins from different species (Reeck et al., (1987) Cell; 50: 667). Such nucleic acid molecules or proteins have sequence homology, as reflected by their sequence similarity, whether in terms of substantial percent similarity or the presence of specific residues or motifs at conserved positions.

Host Cell

The term "host cell" means any cell of any organism that is selected, modified, transformed, grown or used or manipulated in any way for the production of a substance by the cell. For example, a host cell may be one that is manipulated to express a particular gene, a DNA or RNA sequence, a protein or an enzyme. Host cells can further be used for screening or other assays that are described infra. Host cells may be cultured in vitro or one or more cells in a non-human animal (e.g., a transgenic animal or a transiently transfected animal). Suitable host cells include but are not limited to *Streptomyces* species and *E. coli*.

Treating or Treatment

"Treating" or "treatment" of a state, disorder or condition includes:

(1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The benefit to a subject to be treated is either statistically significant or at least perceptible to the patient or to the physician.

Patient or Subject

"Patient" or "subject" refers to mammals and includes human and veterinary subjects.

Therapeutically Effective Amount

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

About or Approximately

The term "about" or "approximately" means within an acceptable range for the particular value as determined by one of ordinary skill in the art, which will depend in part on how the value is measured or determined, e.g., the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Unless otherwise stated, the term 'about' means within an acceptable error range for the particular value.

Dosage

The dosage of the therapeutic formulation will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level.

Carrier

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Isolated

As used herein, the term "isolated" means that the referenced material is removed from the environment in which it is normally found. Thus, an isolated biological material can be free of cellular components, i.e., components of the cells in which the material is found or produced. Isolated nucleic acid molecules include, for example, a PCR product, an isolated mRNA, a cDNA, or a restriction fragment. Isolated nucleic acid molecules also include, for example, sequences inserted into plasmids, cosmids, artificial chromosomes, and the like. An isolated nucleic acid molecule is preferably excised from the genome in which it may be found, and more preferably is no longer joined to non-regulatory sequences, non-coding sequences, or to other genes located upstream or downstream of the nucleic acid molecule when found within the genome. An isolated protein may be associated with other proteins or nucleic acids, or both, with which it associates in the cell, or with cellular membranes if it is a membrane-associated protein.

Mutant

As used herein, the terms "mutant" and "mutation" refer to any detectable change in genetic material (e.g., DNA) or any process, mechanism, or result of such a change. This includes gene mutations, in which the structure (e.g., DNA sequence) of a gene is altered, any gene or DNA arising from any mutation process, and any expression product (e.g., protein or enzyme) expressed by a modified gene or DNA sequence. As used herein, the term "mutating" refers to a process of creating a mutant or mutation.

Nucleic Acid Hybridization

The term "nucleic acid hybridization" refers to anti-parallel hydrogen bonding between two single-stranded nucleic acids, in which A pairs with T (or U if an RNA nucleic acid) and C pairs with G. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994. Ch. 7.

Typically, hybridization of two strands at high stringency requires that the sequences exhibit a high degree of complementarity over an extended portion of their length. Examples of high stringency conditions include: hybridization to filter-bound DNA in 0.5 M $NaHPO_4$, 7% SDS, 1 mM EDTA at 65° C., followed by washing in 0.1×SSC/0.1% SDS at 68° C. (where 1×SSC is 0.15M NaCl, 0.15M Na citrate) or for oligonucleotide molecules washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos)). Accordingly, the term "high stringency hybridization" refers to a combination of solvent and temperature where two strands will pair to form a "hybrid" helix only if their nucleotide sequences are almost perfectly complementary (see Molecular Biology of the Cell, Alberts et al., 3rd ed., New York and London: Garland Publ., 1994, Ch. 7).

Conditions of intermediate or moderate stringency (such as, for example, an aqueous solution of 2×SSC at 65° C.; alternatively, for example, hybridization to filter-bound DNA in 0.5 M $NaHPO_4$, 7% SDS, 1 mM EDTA at 65° C., and washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA and length and base composition of the probe, and are normally determined empirically in preliminary experiments; which are routine (see Southern, J. Mol. Biol. 1975; 98: 503; Sambrook et al., Molecular Cloning: A Laboratory Manual, 2nd ed., vol. 2, ch. 9.50, CSH Laboratory Press, 1989; Ausubel at al. (eds.), 1989, Current Protocols in Molecular Biology, Vol. I, Green Publishing Associates, Inc., and John Wiley & Sons, Inc., New York, at p. 2.10.3).

As used herein, the term "standard hybridization conditions" refers to hybridization conditions that allow hybridization of sequences having at least 75% sequence identity. According to a specific embodiment, hybridization conditions of higher stringency may be used to allow hybridization of only sequences having at least 80% sequence identity, at least 90% sequence identity, at least 95% sequence identity, or at least 99% sequence identity.

Nucleic acid molecules that "hybridize" to any desired nucleic acids of the present invention may be of any length. In one embodiment, such nucleic acid molecules are at least 10, at least IS, at least 20, at least 30, at least 40, at least 50, and at least 70 nucleotides in length. In another embodiment, nucleic acid molecules that hybridize are of about the same length as the particular desired nucleic acid.

Nucleic Acid Molecule

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

Orthologs

As used herein, the term "orthologs" refers to genes in different species that apparently evolved from a common ancestral gene by speciation. Normally, orthologs retain the same function through the course of evolution. Identification of orthologs can provide reliable prediction of gene function in newly sequenced genomes. Sequence comparison algorithms that can be used to identify orthologs include without limitation BLAST, FASTA, DNA Strider, and the GCG pileup program. Orthologs often have high sequence similarity. The present invention encompasses all orthologs of the desired protein.

Operatively Associated

By "operatively associated with" is meant that a target nucleic acid sequence and one or more expression control sequences (e.g., promoters) are physically linked so as to permit expression of the polypeptide encoded by the target nucleic acid sequence within a host cell.

Percent Sequence Similarity or Percent Sequence Identity

The terms "percent (%) sequence similarity", "percent (%) sequence identity", and the like, generally refer to the degree of identity or correspondence between different nucleotide sequences of nucleic acid molecules or amino acid sequences of proteins that may or may not share a common evolutionary origin (see Reeck et al., supra). Sequence identity can be determined using any of a number of publicly available sequence comparison algorithms, such as BLAST, PASTA, DNA Strider, GCG (Genetics Computer Group, Program Manual for the GCG Package, Version 7, Madison, Wis.), etc.

To determine the percent identity between two amino acid sequences or two nucleic acid molecules, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are, or are about, of the same length. The percent identity between two sequences can be determined using techniques similar to those described below, with or without allowing gaps. In calculating percent sequence identity, typically exact matches are counted.

The determination of percent identity between two sequences can be accomplished using a mathematical algorithm. A non-limiting example of a mathematical algorithm utilized for the comparison of two sequences is the algorithm of Karlin and Altschul, Proc. Natl. Acad. Sci. USA 1990, 87:2264, modified as in Karlin and Altschul, Proc. Natl. Acad. Sci. USA 1993, 90:5873-5877. Such an algorithm is incorporated into the NBLAST and XBLAST programs of Altschul et al., J. Mol. Biol. 1990; 215: 403. BLAST nucleotide searches can be performed with the NBLAST program, score=100, wordlength=12, to obtain nucleotide sequences homologous to sequences of the invention. BLAST protein searches can be performed with the XBLAST program, score=50, wordlength=3, to obtain amino acid sequences homologous to protein sequences of the invention. To obtain gapped alignments for comparison purposes, Gapped BLAST can be utilized as described in Altschul et al., Nucleic Acids Res. 1997, 25:3389. Alternatively, PSI-Blast can be used to perform an iterated search that detects distant relationship between molecules. See Altschul et al. (1997) supra. When utilizing BLAST, Gapped BLAST, and PSI-Blast programs, the default parameters of the respective programs (e.g., XBLAST and NBLAST) can be used. See ncbi.nlm.nih.gov/BLAST/on the WorldWide-Web. Another non-limiting example of a mathematical algorithm utilized for the comparison of sequences is the algorithm of Myers and Miller, CABIOS 1988; 4: 11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used.

In a preferred embodiment, the percent identity between two amino acid sequences is determined using the algorithm of Needleman and Wunsch (J. Mol. Biol. 1970, 48:444-453), which has been incorporated into the GAP program in the GCG software package (Accelrys, Burlington, Mass.; available at accelrys.com on the WorldWideWeb), using either a Blossum 62 matrix or a PAM250 matrix, a gap weight of 16, 14, 12, 10, 8, 6, or 4, and a length weight of 1, 2, 3, 4, 5, or 6. In yet another preferred embodiment, the percent identity between two nucleotide sequences is determined using the GAP program in the GCG software package using a NWS-gapdna.CMP matrix, a gap weight of 40, 50, 60, 70, or 80, and a length weight of 1, 2, 3, 4, 5, or 6. A particularly preferred set of parameters (and the one that can be used if the practitioner is uncertain about what parameters should be applied to determine if a molecule is a sequence identity or homology limitation of the invention) is using a Blossum 62 scoring matrix with a gap open penalty of 12, a gap extend penalty of 4, and a frameshift gap penalty of 5.

In addition to the cDNA sequences encoding various desired proteins, the present invention further provides polynucleotide molecules comprising nucleotide sequences having certain percentage sequence identities to any of the aforementioned sequences. Such sequences preferably hybridize under conditions of moderate or high stringency as described above, and may include species orthologs.

Variant

The term "variant" may also be used to indicate a modified or altered gene. DNA sequence, enzyme, cell, etc., i.e., any kind of mutant.

Pharmaceutically Acceptable

When formulated in a pharmaceutical composition, a therapeutic compound of the present invention can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

Pharmaceutically Acceptable Derivative

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

Pharmaceutical Compositions and Administration

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

The compositions of the invention can be formulated for administration in any convenient way for use in human or veterinary medicine. In one embodiment, the one or more exogenous factors, (i.e., active ingredient) can be delivered in a vesicle, including as a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the exogenous factor(s) can be delivered in a controlled release form. For example, one or more exogenous factors, (e.g., Shh) may be administered in a polymer matrix such as poly (lactide-co-glycolide) (PLGA), in a microsphere or liposome implanted subcutaneously, or by another mode of delivery (see Cao et al., 1999, Biomaterials, February; 20(4):329-39). The microspheres of the present invention may also be composed of PLGA and anhydrous poly-vinyl alcohol (PVA). Edlund et al. "Degradable Polymer Microspheres for Controlled Drug Delivery", Advances in Polymer Science Vol. 157, 2002, 67) lists on page 77 a number of different degradable polymers investigated for controlled drug delivery applications (e.g. polyglycolide, polylactide, etc.). Thus, suitable controlled or continuous release formulations useful in the present invention could be made using these other degradable polymers. PVA is one of a range of possible substances that can be used to stabilize microspheres produced by emulsion solvent evaporation techniques. PVA is used as a stabilizing/emulsifying agent. Varying the concentration of PVA can enable the size of the microspheres to be varied, which in turn can influence the release profile (e.g. See, Zhao et al. BioMagnetic Research and Technology 2007, 5:2 "Process and formulation variables in the preparation of injectable and biodegradable magnetic microspheres. PLGA microspheres of the present invention may range in size from 10-40 µm, with an average diameter of 20 µm. The size can be controlled by varying the speed of the homogenizer, etc. In certain embodiments, larger particles may be used; varying the size of the microspheres can be guided by clinical considerations. The degradation of microspheres is based on the hydrolysis of the ester linkages in the PLGA polymer. In general, biodegradable polymers have been classified into surface-eroding and bulk-eroding (See Biomaterials, 2002, 23:4221-4231). PLGA is reported to be a bulk-eroding polymer (Id.). As described in the Examples, exemplary pharmaceutical formulations of the present invention have achieved release of biologically active Shh from microspheres over a 7 day period, with an indication that Shh continues to be released for a time beyond the 7 day test period.

Another aspect of delivery includes the suspension of microspheres in an alginate hydrogel, which is considered biocompatible and is compatible with stem cells. The bioactive factor would be released from the microsphere present in the hydrogel; therefore, its rate of release can be adjusted in the same way as when there is no hydrogel (e.g., by changing the composition/molecular weight of polymers used to make the microsphere, changing protein loading in the microsphere, microsphere size, etc.). It was shown in Ashton et al., that the incorporation of microspheres containing alginate lyase into the hydrogel enable controlled release of this enzyme which in turn provides control over the rate of degradation of the hydrogel (Ashton et al. 2007; Piantino et al., 2006, Exp Neurol., 201(2):359-67; See also, U.S. Pat. No. 7,226,617 to Ding et al. Yet another aspect of the invention includes the use of nanoparticles for the delivery of exogenous factors to nervous system sites. Another example of controlled release compositions include an amorphous carbohydrate glass matrix, as described in detail in PCT publication number WO 93/10758, in which a bioactive agent such as Shh is incorporated into the carbohydrate glass matrix and controlled release or degradation is adjusted by addition of a hydrophobic substance.

In certain embodiments, the microspheres of the present invention are, injected at the site of spinal cord injury. For injections into the spinal cord, a 1 µl microsphere suspension containing 0.13 mg microspheres per µl media is used. In certain embodiments, the microspheres are loaded with 0.65 µg of Shh (recombinant human Shh from R&D Systems, Minneapolis, Minn., corresponding to SEQ ID NO:2, the active N-terminal Shh fragment (Cys24-Gly 197 of SEQ ID NO: 1) per µl of microsphere suspension. In a preferred embodiment, the microspheres of the present invention release bioactive levels of at least one exogenous factor, e.g., from about 1 ng/ml to about 20 ng/ml Shh, more preferably from about 1 ng/ml to about 10 ng/ml Shh, and most preferably from about 2 ng/ml to about 7 ng/ml Shh. In certain embodiments, microsphere compositions of the present invention release a preferred concentration of about 5 ng/ml Shh over a course of at least about 7 days. In the present invention, any controlled release formulation may be used in lieu of microspheres that have a similar controlled release profile (e.g., releasing at least one exogenous factor in the preferred range over a course of at least about 7 days).

In yet another embodiment, one or more additional exogenous factors either alone, or in combination with Shh can include, but is not limited to, any one or more of the following components loaded within a nanosphere/microsphere or other controlled release formulation: enzymes, proteins, and antibodies. For example, neurotrophic molecules, such as Nerve Growth Factor (NGF), Brain-Derived Neurotrophic Factor (BDNF), Neurotrophin (NT) 3, 4/5, and 6, Ciliary Neurotrophic Factor (CNTF), Glial Cell Line-Derived Growth Factor (GDNF), Leukemia Inhibitory Factor (LIF), Interleukin 6 (IL6). Interleukin 11(IL11), and Cardiotrophin 1, and growth factor hormones, epidermal growth factor (EGF) such as interferon-α (IFNa), Interferon (IFN) and Tumor Necrosis Factor (TNF), e.g. TNF-α, can be incorporated into the nanospheres/microspheres or other controlled release formulation of the present invention. Further, proteoglycans, such as decorin, or antibodies that block the inhibitory activity of certain proteoglycans (such as NG2 proteoglycan) can further be incorporated into the nanospheres/microspheres or other controlled release formulations of the present invention. Carrier proteins, such as Bovine Serum Albumin (BSA), Keyhole Limpet Hemocyanin (KLH), Ovalbumin (OVA), Fetal Bovine Serum (FBS), Thyroglobulin (THY), and Human Serum Albumin (HSA), can optionally be loaded into the controlled release formulation of the present invention. Any combination of these nanosphere/microsphere or other controlled release formulation loaded factors, including Shh with any of these additional factors, can also be combined with stem cells in the present invention.

In certain embodiments of the present invention, a first exogenous-factor-containing microsphere or nanoparticle suspension, or other controlled release formulation, containing at least one exogenous factor, may be used in combination with a second controlled release formulation (e.g., a second microsphere suspension), containing at least one exogenous factor that is different than that contained in the first controlled release formulation. Such an approach may be termed "combinational therapy" and is useful for the treatment of diseases and conditions as described herein. For example, combinational therapy may be used for the treatment of spinal cord injury (SCI). SCI involves glial scar formation, loss of cells and slow dying of remaining cells. Using a combination approach, a first controlled release formulation (e.g., a first set of a microspheres) may be loaded with scar-chewing enzymes, such as, e.g., chondroitinase ABC (CABC) or hyaluronidase (Struve et al, Glia, 2005) and a second controlled release formulation may be loaded with, e.g., Shh to promote growth, or with GDNF to reduce cell death. In other embodiments, these and/or other factors may be combined in a single controlled release formulation or each in separate formulations (e.g., a separate suspension of microspheres or nanoparticles for each factor to be administered to a nervous system site).

These sustained or controlled release formulations or mixtures of combinations of controlled release formulations of the present invention are delivered by injection at the site of injury or site where increased neural cell growth is desired. Optionally, a second injection is delivered rostral to the first injection site (1 mm for the mouse models, for humans the distance may be adjusted according). In certain embodiments, the formulation(s) may also be administered systemically, e.g., intravenously. In yet other embodiments, the controlled release formulations each containing at least one exogenous factor as described above are also loaded with NSC or endothelial-expanded NSC and, optionally, retinoic acid.

In certain embodiments of the present invention, retinoic acid (RA) is included in a controlled release composition, such as microspheres. RA is known to induce differentiation of P19 cells into neurons, astrocytes and oligodendrocytes, cell types which are normally derived from the neuroectoderm. P19 cells are an embryonal carcinoma cell line having many characteristics of embryonic stem cells, including an ability to differentiate into different cell types (e.g., skeletal muscle, cardiac muscle and neurons). Newman, K. D, and M. W. McBurney (2004) Biomaterials 25:5763-5771, describes including RA and P19 cells in PLGA microspheres.

Other examples of exogenous factors include basic fibroblast growth factor (bFGF), hyaluronidase, and insulin-related growth factor (IGF-I). Other growth factors and combinations of growth factors and/or scar-digesting enzymes that are useful for promoting growth and differentiation of NSC into nervous system cells and/or for decreasing scar formation, are contemplated by the present invention. For examples of combinational therapy, see e.g., Schwab J M, et al. (2006) Prog. Neurobiol.; 78(2):91-116; Pearse D D and Bunge M B. (2006) J. Neurotrauma; 23(3-4):438-52; Azanchi R, et al. (2004) J. Neurotrauma; 21(6):775-88; Kim B G, e al. (2008) J. Comp. Neurol.; 508(3):473-86; and Bretzner F, et al. (2008) Eur J Neurosci. (9): 1795-807.

In one embodiment, the PLGA microspheres are prepared containing bioactive morphogenic or growth factor (e.g., recombinant human Shh from R&D Systems, Minneapolis, Minn., corresponding to SEQ ID NO:2, the active N-terminal Shh fragment (Cys24-Gly 197 of SEQ ID NO:1). In another embodiment, the microspheres may contain Mg hydroxide to neutralize acids generated during PLGA degradation (See, Zhu et al. Nature Biotech, January 2000, Vol. 18(1):52-57) and/or as a cryoprotectant to improve protein stability. (See, Jaganathan et al. International J. of Pharmaceutics, 2005, 294: 23-32).

Preferably, the controlled release formulations of the present invention release bioactive levels of at least one exogenous factor, e.g., Shh, for at least about 7 days. In some embodiments, the controlled release formulations release bioactive amounts of at least one exogenous factor for at least about 2 weeks. The amount of exogenous factor released and the duration of release may be determined by an in vitro assay, as described in Example 1, infra. The extent and duration of release from microspheres may be controlled by varying parameters such as polymer molecular weight, composition, microsphere size, and protein loading (See, Freiberg et al. "Polymer Microspheres for controlled drug release," International J. of Pharmaceutics, 2004 282: 1-18; Berkland et al. "PLG Microsphere Size Controls Drug Release Rate Through Several Competing Factors" Pharm. Res. 2003, 20:1055-1062; and Ashton et al. describing the effects of varying protein loading in the microsphere).

The effective amounts of compounds of the present invention include doses that partially or completely achieve the desired therapeutic, prophylactic, and/or biological effect. The actual amount effective for a particular application depends on the condition being treated and the route of administration. The effective amount for use in humans can be determined from animal models. For example, a dose for humans can be formulated to achieve circulating and/or local concentrations that have been found to be effective in animals.

Kits

In one embodiment, the invention relates to a kit comprising an effective amount of a sustained delivery composition comprising one or more exogenous factors useful for increasing neuronal cell growth or treating spinal cord or nervous system injuries, and optionally stem cells packaged in a manner suitable for administration to a patient. In certain embodiments, the kits also include instructions teaching one or more of the methods described herein.

The abbreviations in the specification correspond to units of measure, techniques, properties or compounds as follows: "min" means minutes, "h" means hour(s), "μL" means microliter(s), "mL" means milliliter(s), "mM" means millimolar, "M" means molar, "μl" means microliter(s); "mmole" means millimole(s), "kb" means kilobase, "bp" means base pair(s), and "IU" means International Units. "Polymerase chain reaction" is abbreviated PCR; "Reverse transcriptase polymerase chain reaction" is abbreviated RT-PCR; "Estrogen receptor" is abbreviated ER; "DNA binding domain" is abbreviated DBD; "Untranslated region" is abbreviated UTR; "Sodium dodecyl sulfate" is abbreviated SDS; and "High Pressure Liquid Chromatography" is abbreviated HPLC.

EXAMPLES

Materials and Methods

The following describes the materials and methods employed in Examples 1-6.

Animals

The care and use of animals reported in this study was approved and overseen by Taconic Farms, which is licensed by the US Department of Agriculture and the New York State Department of Health, Division of Laboratories and Research and accredited by the American Association for the Accreditation of Laboratory Animal Care. Mice are purchased from Taconic Farms and are either Swiss Webster or C57-BL6.

Cell Culture

Mouse embryonic day 8-9 (E8-9) spinal cords (Swiss Webster, Taconic Farms, or GFP transgenic mice from Jackson labs on a C57BL6 background) were dissected and enzymatically dissociated using papain (Worthington) as described previously (Qian et al. 1997). Briefly, spinal cord tissue was incubated in 5-7 units/ml activated papain solution plus 32 μg/ml DNase in DMEM with rocking for 20 minutes at room temperature. The tissue was rinsed 3 times with DMEM (Gibco) and triturated with a fire-polished glass Pasteur pipette to generate a single-cell suspension. Cells were plated at clonal density (2000-4000 cells/well) onto poly-L-lysine coated 6-well plates and cultured in basal serum-free medium consisting of DMEM with L-glutamine, sodium pyruvate, B-27, N-2 (Stem Cell Inc.), 1 mM N-acetylcysteine (Sigma) and 10 ng/ml bFGF (Gibco), and 10 ng/ml LIF (Sigma).

For co-culture expansion for transplantation experiments, bovine pulmonary artery endothelial (BPAE) cells (VEC Technologies INC., ATCC. #CCL-209) were used at passage 10-20. Three days before co-culturing with spinal cord cells, endothelial cells were plated into 60 mm transwell membrane inserts (Costar) at 2000 cells/transwell, in DMEM with 10% FBS. Four hours before use, the transwells were rinsed and transferred to serum-free medium containing 10 ng/ml FGF2. The transwells containing feeder cells were placed above freshly plated, low density cultures of spinal cord cells, and the co-cultures were fed every two days with serum-free medium, cells were co-cultured in 6-well plates with BPAE cells. One μM Shh N terminal peptide (R&D systems, SEQ ID NO:2) and 1 μM retinoic acid (RA) (Sigma) were added to the cultures.

Preparation of Cells for Transplantation

On the day of surgery, the cells were removed from the wells with Accutase, centrifuged, washed with HBSS, centrifuged, dissociated into single cells, resuspended in culture media, and counted. The concentration of viable cells (usually greater than 90%), as determined by Trypan blue exclusion, was adjusted to 105 cells/μl. The cells were maintained on ice until use.

Surgical Procedures and Experimental Groups

Adult (10-12 week (wk) old) female C57BL/6 mice were deeply anesthetized by inhalation of isoflurane vapor (3%). The surgery was performed as described previously (Li et al. 2005). A complete laminectomy was performed and the dorsal aspect of the spinal cord was exposed at T8 and T9 levels. A dorsal over-hemisection was performed at T8 using a pair of microscissors and a scalpel blade to completely sever the dorsal and dorsolateral corticospinal tracts. The depth of the lesion (1.0 mm) was assured by passing a marked needle across the dorsal pan of the spinal cord. The lesion was bilaterally symmetric and extended to a depth about two thirds of the dorso-ventral axis of the spinal cord. 0.5 μl of cells or 0.5 μl of microspheres, or a mix of cells and microspheres were slowly injected into the site of the injury and into a second site 1 mm rostral to the injury site. After surgery, animals were maintained on heating pads, closely observed until fully awake and then returned to their home cages. Mice were allowed to recover for 4 weeks.

Experimental groups were as follows: 1) Control microspheres (n=6); 2) Control microspheres+endothelial expanded untreated cells (n=8); 3) Shh microspheres+endothelial expanded untreated cells (n=7); 4) Shh microspheres+endothelial expanded Shh treated cells (n=5); 5) Shh microspheres (n=6). In the figures, "microspheres" is abbreviated "μs."

Behavioral Testing

Horizontal Ladder Walking Test

This test assesses the ability to accurately place the hind paws while walking on a horizontal ladder by analyzing the frequency of failure to accurately grasp the rungs. The ladder apparatus (adapted from (Metz and Whishaw 2002)) is 23 inches long, and consists of side walls made of clear Plexiglas® and metal rungs that could be inserted with minimal spacing of ⅜ inch. The ladder was elevated 30 cm above the ground with a refuge (home cage) at the end. The mice were videotaped and scored at a later date by an experimenter blind to the treatment groups. The number of foot-slips per run was recorded (as shown in FIG. 2A).

Open Field Locomotion—Basso Mouse Scale Test

This test assesses body coordination, trunk stability, and locomotion (Basso et al. 2006). Mice are placed on a smooth surface table and their walk is videotaped. Movies are scored by an experimenter blind to the treatment groups (as shown in FIG. 2B).

Rearing Test

This test assesses hind limb strength. Mice are placed in a glass cylinder and allowed to explore their environment.

Rearing is graded as: 0—mouse supports its weight on full plantar surface, heel does not leave the ground: 1—mouse supports its weight on toes, heel rise above the ground; 2—mouse is capable of supporting its weight on tiptoes. The mice were videotaped and scored at a later date by an experimenter blind to the treatment groups (as shown in FIG. 2C).

Swim Test

This test assesses hind limb movement, forelimb dependency, hindlimb alteration, trunk instability and body angle as described in Smith R R, et al. (2006) J Neurotrauma. (11):1654-70. Mice were placed in a Plexiglas® chamber that is 60 inches long, 7 inches wide, and 12 inches deep. An adjustable Plexiglas® ramp, placed at one end of the chamber and covered with a 5 mm-thick, soft neoprene pad, allows animals to exit the pool. The pool is filled to a depth of 8 inches with warm tap water (27-30° C.) for each swimming session and is thoroughly cleaned daily. Hind limb movement, forelimb dependency, hindlimb alteration, trunk instability and body angle were each graded as described in Smith R R, Burke D A, Baldini A D, Shum-Siu A, Baltzley R, Bunger M, Magnuson D S. The Louisville Swim Scale: a novel assessment of hindlimb function following spinal cord injury in adult rats. J Neurotrauma. 2006 November; 23(11):1654-70. Asterisks indicate p<0.01. The mice were videotaped and scored at a later date by an experimenter blind to the treatment groups (as shown in FIG. 2D).

Tape Removal Test

Figure 6C:
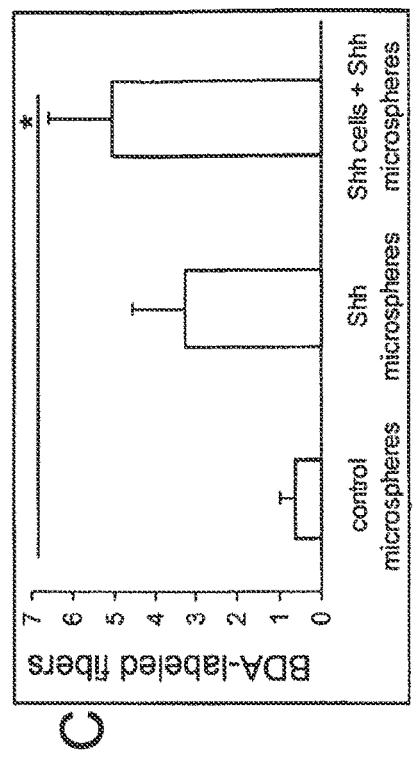
FIGS. 6A-C show that transplantation of Shh-containing microspheres into the site of SCI promotes corticospinal tract fiber sprouting and growth in the caudal spinal cord.

The tape removal test was used to assess both sensory impairment and paw function. Mice were scruffed and held by one experimenter while another placed strips of tape (⅛ inch×0.5 inch; Fisherbrand) over the ventral surface of the hindpaw. The mouse was placed on a smooth surface, and the timer was started. The time taken for the mouse to notice the tape (touch the tape with the snout) was noted. The animals were given a maximum of 3 minutes to sense the tape. The mice were videotaped and scored at a later date by an experimenter blind to the treatment groups (as shown in FIG. 6C).

Immunocytochemistry

Cell cultures were fixed with 4% paraformaldehyde in PBS (140 mM NaCl, 2.6 mM KCl, 8 mM $Na_2HPO_4$, 1.4 mM $KH_2PO_4$ pH 7.4) for 30 minutes and rinsed three times with PBS buffer at pH 7.4. Cells were incubated with 10% normal goat serum (NGS) in PBS with 0.1% Triton X-100 (PBST) for 30 min. No Triton X-100 was used when cells were immunolabeled with O4, an antibody against a surface membrane protein. Primary antibodies (Table 1) were added and incubated overnight at 4° C., followed by three rinses with PBS, and then a one hour incubation with the appropriate secondary antibodies. Alexa-conjugated secondary antibodies (goat anti-rabbit IgG and goat anti-mouse IgM and IgG, Invitrogen) were used at 1:500 dilution.

TABLE 1

Primary antibodies

| Antibody | Expression | Species, isotype | Dilution | Source |
|---|---|---|---|---|
| β-tubulin III | Neurons | Mouse IgG2b | 1:600 | Sigma |
| GFAP | Astrocytes | Rabbit IgG | 1:1000 | Dako |
| Ki67 | Dividing cells | Rabbit IgG | 1:1000 | Vector labs |
| Nestin | Embryonic progenitors | Mouse IgG1 | 1:4 | DSHB |
| NeuN | Neurons | Mouse IgG1 | 1:100 | Chemicon |
| O4 | Oligodendrocytes | Mouse IgM | Neat | DSHB |
| RIP | Oligodendrocytes | Mouse IgG1 | 1:50 | DSHB |

Cryostat Sections

Mice were deeply anesthetized and perfused transcardially with 4% paraformaldehyde in 0.1 M phosphate buffer (PB) solution, pH 7.4. Spinal cord segments containing the injury sites were dissected, rinsed in 0.1 M PB solution, and placed into 0.1 M PB solution containing 30% sucrose for 24 h at 4° C. The spinal cord tissue was then frozen in embedding media (O.C.T. compound, Tissue-Tek) and serially sectioned on a cryostat (20 μm sections). Tissue sections were washed in PBS and incubated for 10 min with 10% normal goat serum (NGS) in PBS with 0.3% Triton X-100. The sections were then incubated with the appropriate primary antibody (Table 1) overnight in 10% NGS-PBST at 4° C. The following day, sections were washed three times (5 min each) in PBS and incubated with appropriate secondary antibodies for 1 hour.

Preparation of Bioactive Biodegradable Microspheres

Generally, the microspheres were prepared from poly (lactide-co-glycolide) PLGA (Boehringer Ingleheim) and Shh aseptically using the double emulsion method at room temperature. Shh microspheres (10-40 μm in diameter) containing 0.5% Shh (Cat. No. 1314-SH/CF, recombinant human Shh from R&D Systems, Minneapolis, Minn., corresponding to SEQ ID NO:2, the active N-terminal Shh fragment, which corresponds to Cys24-Gly 197 of SEQ ID NO: 1), as well as control PLGA microspheres without any incorporated Shh protein were prepared. An aqueous solution of 3.125 μg of Shh was suspended in 625 μg of PLGA dissolved in methylene chloride. This solution was sonicated for 3 s at 20% amplitude in an ice bath using a Vibra-Cell™ high-intensity ultrasonic liquid processor (Sonics & Materials, Inc.) to form a first water/oil emulsion. This emulsion was then dispersed and stabilized in 20 ml of 0.5% (w/v) aqueous polyvinylalcohol (PVA), and mixed at high speed (8000 rpm) with a Silverson L4RT high shear laboratory mixer, ¾ inch tip, for 20 sec to produce the second water/oil/water emulsion. This emulsion was stirred for 1 hour at room temperature allowing the microspheres to form by evaporation of methylene chloride. The microspheres were then isolated by centrifugation (1500 rpm, 3 min) and subsequently washed four times with distilled deionized water to remove adsorbed PVA. To remove water, the microspheres were collected by centrifugation, frozen in liquid nitrogen, and lyophilized. The dried microspheres were stored in a sealed glass vial and placed in a dessicator at −20° C. The morphology and size of the microspheres were characterized by scanning electron microscopy. Double-emulsion techniques used in the present invention are a variation of those described in (Fu et al. 2003).

Statistics

Behavioral scores for all animals in each group were averaged, the standard deviation and the standard error of the mean were calculated, and all statistical analyses were performed using Microsoft Excel software. BDA fibers were counted from at least five sections for each treatment. The numbers of fibers for each experiment were averaged, the standard deviation and the standard error of the mean were calculated, and all statistical analyses were performed using Microsoft Excel software.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Shh-Containing Microspheres Release Active Shh Protein In Vitro and are not Toxic to Neural Stem Cells.

To establish a source of continuous release of Shh, biodegradable microspheres (10-40 µm in diameter) of poly (lactide-co-glycolide) (PLGA) that incorporated 0.5% of Shh as described above (Cat. No. 1314-SH/CF, recombinant human Shh from R&D Systems, Minneapolis, Minn., corresponding to SEQ ID NO:2, the active N-terminal Shh fragment, which corresponds to Cys24-Gly 197 of SEQ ID NO: 1) were generated. Microsphere preparation is described above and adapted from the methods of (Fu et al. 2003). To determine the release kinetics 0.1 mg of Shh-containing microspheres or microspheres with PLGA alone (blank sample) were resuspended in 1 ml PBS. 100 µl aliquots were taken out each day and analyzed for the Shh release by ELISA, as shown in FIG. 1A. FIGS. 1A-B show biodegradable PLGA-based microspheres release active Shh in a course of at least 7 days. These microspheres are not toxic for neural stem cells In FIG. 1A, 0.5% Shh microspheres were resuspended in PBS. 100 µl aliquotes were analyzed daily for Shh release by ELISA. No Shh was released in the PLGA alone group, and thus, these zero data points do not appear on the graph in FIG. 1A. The amount of Shh measured in each aliquot from the Shh-containing microspheres group is graphed in FIG. 1A (data points are represented by circles). This preparation of microspheres was found to continuously release about 5 ng/ml Shh per day in a course of at least 7 days.

Although the present examples have been conducted with this microsphere composition, it is contemplated that any biologically acceptable sustained release composition that can continuously release the desired amount of one or more exogenous factors, (e.g., at least about 5 ng/ml Shh per day in a course of at least 7 days) would be useful in the present methods. Suitable compositions include for example liposomes, alginate hydrogels, sustained release nanoparticle compositions, and amorphous carbohydrate glass matrix compositions.

To test whether microsphere-released Shh is bioactive, Shh released from the microspheres in culture with spinal cord stem cells was tested. Spinal cord tissue was dissected from embryonic day 9 (E9) mice, dissociated to single cells and plated at clonal density in Terasaki plates (Nunc 60 well plates purchased from Krackeler Scientific Inc.). Shh-releasing microspheres and control microspheres (PLGA only) were resuspended in BPAE-conditioned medium. Freshly isolated E9 spinal cord NSCs were treated daily with Shh protein or supernatant from control or Shh-releasing microspheres for 5 days. On day 6 cultures were fixed and stained, as shown on FIG. 1B. It was found that spinal cord stem cells cultured with supernatant from suspended control microspheres displayed similar rates of growth/apoptosis as cells cultured in conditioned medium alone (control cells); therefore PLGA microspheres are not toxic for spinal cord stem cells. To further prove this point spinal cord stem cells were cultured with PLGA microspheres added directly to the cells, and similarly a lack of toxicity from the microspheres was observed, as shown in FIG. 1B. In FIG. 1B, White bar=20 µm.

Spinal cord stem cells cultured with Shh protein and spinal cord stem cells cultured with supernatant from Shh-containing microspheres demonstrated increased proliferation and neurogenesis compared to untreated cells or cells treated with the supernatant from control microspheres, as shown in FIGS. 2A-L. In FIGS. 2A-L, the cultured NSCs were immuno-stained for nestin (which identifies progenitor cells FIGS. 2A-D), β-tubulin III (which stains neurons, FIGS. 2E-H), and DAPI (which stains the cell nucleus, FIGS. 2I-L). Positive staining is indicated by bright spots in each cell culture panel.

Example 2

Transplantation of Shh-Releasing Microspheres or a Combination of Shh-Treated Spinal Cord Neural Stem Cells with Shh-Releasing Microspheres Produced/Resulted in Motor Recovery.

Shh-releasing microspheres and a combination of Shh-releasing microspheres and endothelial-expanded Shh treated cells were examined as treatments for SCI. To generate endothelial-expanded spinal cord stem cells, E9 mouse spinal cord stem cells were co-cultured with BPAE cells in serum-free medium with or without the addition of 1 µM Shh and 1 µM retinoic acid for 6 days, then removed and injected into adult (10-12 weeks old) mice recipients that had a dorsal over-hemisection spinal cord injury.

Adult mice were anaesthetized and the dorsal surface of the cord was exposed at T8-9, and the cord was cut down to a depth of 1 mm, representing halfway through the cord from the dorsal surface. This procedure severs the descending corticospinal and ascending sensory spinal axons located in the dorsal columns of the spinal cord (Li et al. 2005; Vallieres et al. 2006). Immediately after the injury was created, microspheres with or without endothelial-expanded E9 mouse spinal cord stem cells were transplanted into the site of the injury. Experimental groups were as follows: 1) Control (PLGA only) microspheres (n=6); 2) Control microspheres+endothelial-expanded untreated E9 mouse spinal cord stem cells (n=8); 3) Shh microspheres+endothelial expanded untreated E9 mouse spinal cord stem cells (n=7); 4) Shh microspheres+endothelial expanded Shh treated E9 mouse spinal cord stem cells (n=5); 5) Shh microspheres (n=6).

Figure 3D:
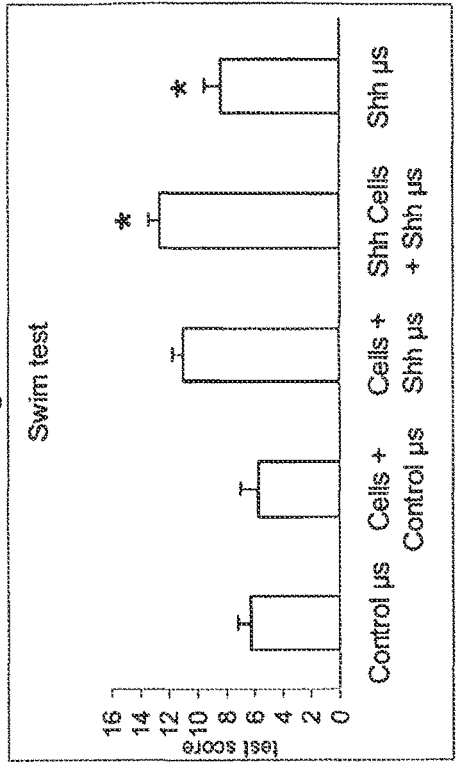
Figure 3A:
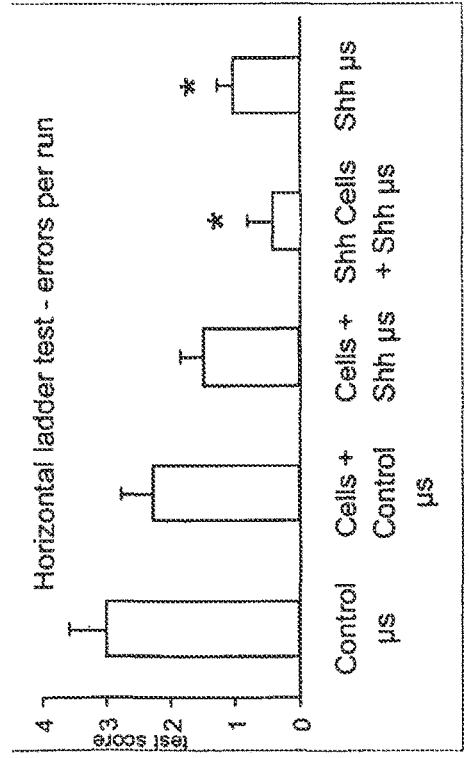
Figure 3C:
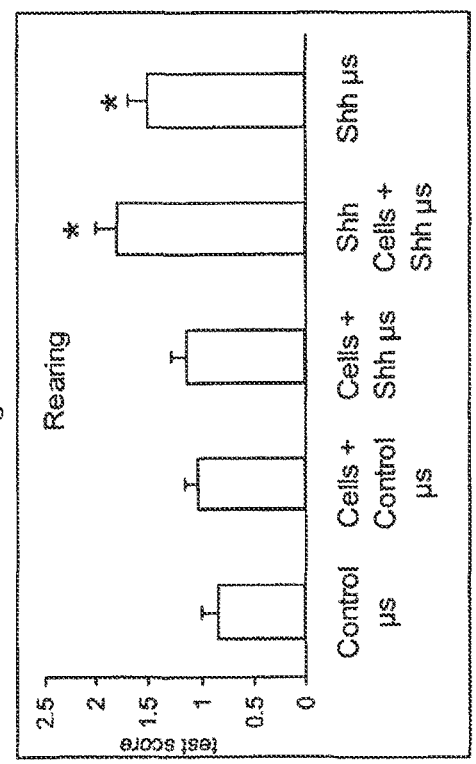

The mice were allowed to recover, all of them were ambulatory after the injury (given that the ventral cord was intact) but had detectable hind paw deficits. After 4 weeks, the motor behaviors of the mice were assessed. Four behavioral tests were used: the skilled horizontal ladder walking test (FIG. 3A), which can detect hind paw deficits (Metz and Whishaw 2002), open field locomotion (Basso Mouse Scale) (FIG. 3B) (Basso et al. 2006), a rearing test to determine hind leg strength (FIG. 3C), and a swim test, which can be used to determine hind limb movement, forelimb dependency, hindlimb alteration, trunk instability and body angle (FIG. 3D). For horizontal ladder test the number of footslips was scored. All the behavioral tests showed a statistically significant motor improvement (*=p≤0.01) between mice that had been treated with Shh-releasing microspheres or a combination of Shh-treated endothelial-expanded spinal cord stem cells and Shh-releasing microspheres versus mice that received control microspheres, as shown in FIG. 3A-D (data shown as mean±SEM).

Mice that received control microspheres had hindpaw deficits comparable to control mice that had a spinal cord injury without a cell transplant (mock injury control). These data (FIGS. 3A-D) point to the benefit, i.e., functional recovery after treating SCI model mice with Shh-releasing microspheres and a combination of Shh-releasing microspheres and spinal cord stem cells that were treated with Shh during their expansion phase ex vivo.

Example 3

Injection of Shh-Releasing Microspheres into SCI Resulted in a Reduced Astroglial Scar Formation Compared to Injection of Control Microspheres into SCI.

Figure 4B:
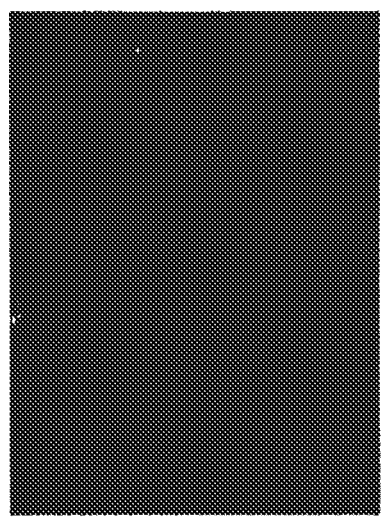
FIGS. 4A-B show that injection of Shh-containing microspheres into mice at site of SCI results in reduced astroglial scar formation.
Figure 4A:
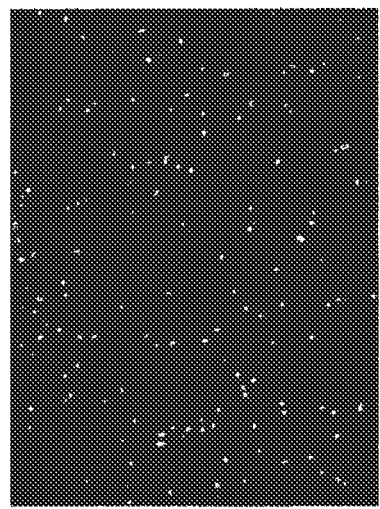

After behavioral testing, the mice were sacrificed (four weeks after SCI) and the spinal cords were examined by staining longitudinal sections of the SCI site with GFAP, which is an astrocyte marker (as shown in FIG. 4A). In FIGS. 4A-B, the spinal cord cells appear as bright regions, since they are isolated from GFP transgenic mice and constitutively express green fluorescent protein (GFP). Transplantation of Shh-releasing microspheres resulted in a decrease of the astrocytic scar at the site of injury, as shown in FIG. 4B, demonstrated by reduced staining of GFAP in FIG. 4B (few bright-staining cells on sections treated with Shh-releasing microspheres) compared to FIG. 4A (control microspheres lacking Shh and containing more brighter staining regions). These data illustrate that injection of Shh-releasing microspheres into SCI site resulted in reduced astroglial scar formation compared to injection of control microspheres.

Transplanted Neural Stem Cells Grafted Well in all Experimental Groups. (FIGS. 5A-I)

The fate of the transplanted cells in the spinal cords of mice was also analyzed by staining longitudinal sections of the SCI site with the astrocyte marker GFAP (middle row, FIGS. 5B, B, and H) and the oligodendrocyte marker RIP (lower row, FIGS. 5C, F, and I). The transplanted cells were visualized by GFP fluorescence. The transplanted cells were found to have survived, and the graft size was approximately the same in all experimental groups. Untreated expanded spinal cord NSCs transplanted alone are known to differentiate mostly into astrocytes. Thus, the addition of control microspheres to untreated expanded spinal cord NSCs should not alter this differentiation pathway. Consistent with this theory, untreated endothelial-expanded spinal cord NSCs co-transplanted with control microspheres differentiated mostly into astrocytes, and not into oligodendrocytes (FIG. 5, A-C, left column). However, when untreated NSCs were instead co-transplanted with Shh-releasing microspheres, the cells differentiated largely into oligodendrocytes (FIG. 5D-F, center column). Furthermore, when Shh-treated NSCs were co-transplanted with Shh-releasing microspheres, the cells also differentiated into oligodendrocytes (FIG. 5G-I, right column). Thus, the Shh released by the microspheres (and not the microspheres themselves) diverted or drove spinal cord NSC differentiation from the astrocyte lineage (undesirable) to the desired oligodendrocyte lineage. Positive staining is indicated by brighter spots or regions of the cell sections.

This effect is believed to be the result of Shh acting in a time and concentration-dependent manner on spinal cord progenitor cells: early in development high concentration of Shh promote NSC differentiate into floor plate, slightly lower amounts promote differentiation into neurons, in development Shh promotes NSC differentiation into oligodendrocytes. In additional experiments, the cell fate of the implanted Shh-treated cells treated with Shh-releasing microspheres is determined by staining the cells' with the neuronal marker NeuN, six weeks after transplantation.

Example 4

Transplantation of Shh-Containing Microspheres into SCI Site Induces CST Fiber Sprouting and Growth in the Caudal Spinal Cord.

Figure 6A:
Figure 6B:
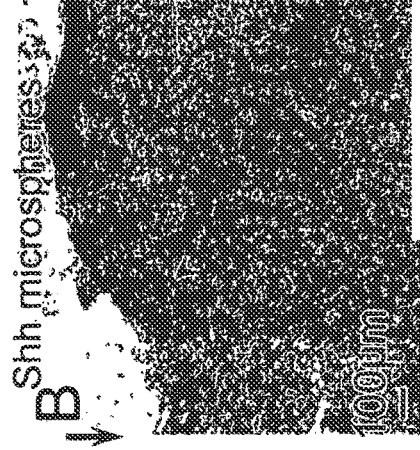

To address the mechanism for the motor recovery in animals that have received Shh-releasing microspheres and a combination of Shh-releasing microspheres and Shh-treated endothelial-expanded cells the corticospinal tract (CST) was analyzed by labeling the fibers of the CST with biotinylated dextran amine (BDA) injections. In mice that received control microspheres, no BDA-labeled CST fibers extended beyond the injury site (FIG. 6A, arrow indicates injury site). However, in mice that received Shh-releasing microspheres, regenerating axons from the transected CST bypassed the transection site and projected into the caudal spinal cord. Sprouting, branched fibers of the CST could be observed in white and gray matter in the caudal spinal cord, as shown in FIG. 6B (see arrowheads). In FIG. 6B, inset shows a magnified image of branched fibers. Axonal sprouting rostral to the lesion site was also enhanced in the animals that received Shh-releasing microspheres and especially in the animals that received a combination of Shh-releasing microspheres and Shh-treated endothelial-expanded cells. The number of BDA-positive fibers (sprouting and growing fibers) was counted 3 mm caudal to the site of SCI. The average number of fibers±SEM per section is shown (FIG. 6C). Results from both the Shh microspheres and Shh-treated NSCs+Shh microspheres groups were significantly different than the control microsphere group (p<0.05 for Shh microspheres and p<0.01 for Shh-treated NSCs+Shh microspheres).

Example 5

Transplantation of Shh/RA-BPAE-Expanded NSC into SCI Site Results in Enhanced Oligodendrocyte Differentiation and Functional Recovery.

To address the role of Shh/RA-endothelial (BPAE)-expanded NSC in the recovery from SCI, these cells were transplanted into the spinal cord following surgical induction of SCI and compared to mice that were transplanted with control cells (BPAE-expanded cells grown without Shh/RA). FIG. 7A is a photograph of a mouse in the horizontal ladder test, the results of which are shown in FIG. 7B. The number of footslips per run was scored for mice that received Shh-endothelial (BPAE) expanded spinal cord cells (n=3) and saline injection controls (n=5). Mice that received BPAE-expanded cells grown without Shh (n=6) behaved as saline injection controls. FIG. 7C shows the results of the tape removal test. The time taken for mice that had been transplanted with Shh/RA-BPAE-expanded NSC at the site of SCI to sense the tape placed on the ventral surface of the hindpaw and to attempt to remove the tape was measured. Both assays show that mice receiving Shh/RA-BPAE grown cells had improved sensory and motor scores compared to saline injection controls. The asterisk indicates that p<0.01.

Example 6

Combinational Therapy

Figure 8:
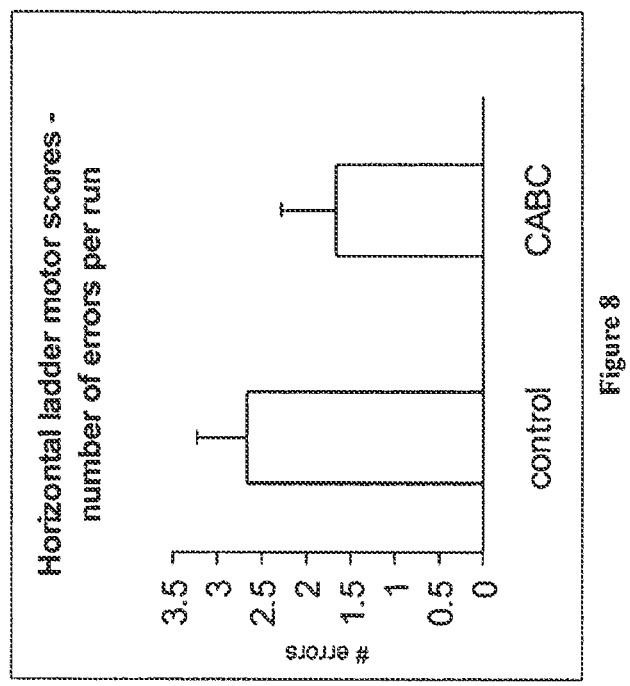
FIG. 8 shows motor recovery after transplantation of CABC containing microspheres into the site of SCI.
Figure 9:
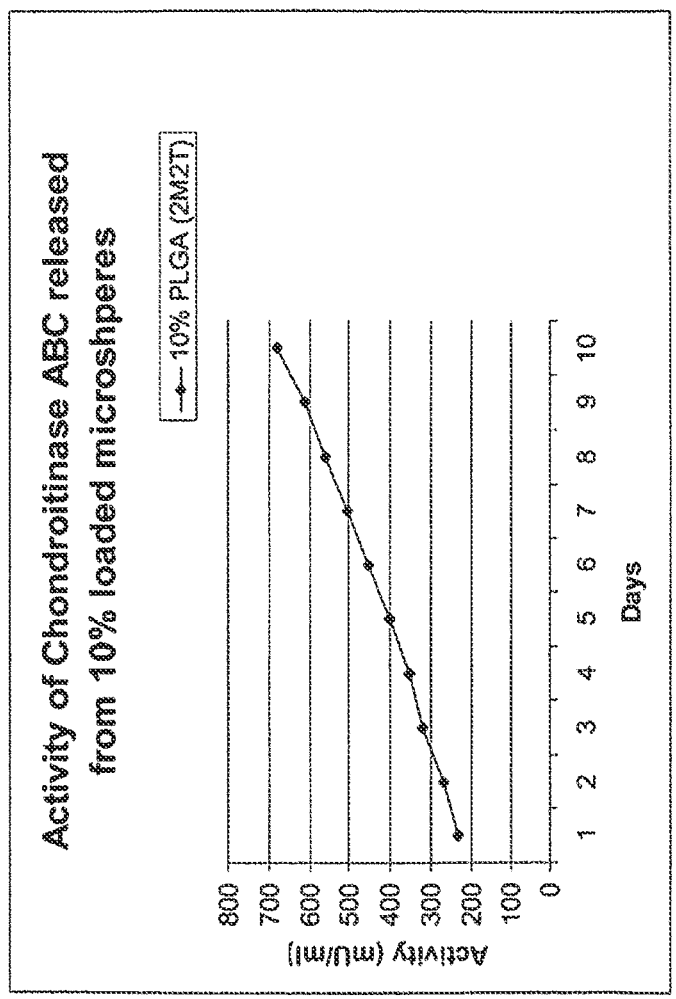
FIG. 9 shows activity of CABC released from 10% loaded PLGA microspheres.

To address the role of CABC in the recovery from SCI, 10% CABC formulation encapsulated in microspheres was transplanted into the mouse spinal cord injury model, Four weeks after the transplantation, animals had shown some motor recovery. However, this recovery had not reached statistically significant levels. These results are shown in FIGS. 8 and 9. FIG. 8 shows transplantation of microspheres releasing chondroitinase ABC into the mouse SCI model resulted in moderate behavioral improvement. The results in FIG. 8 were scored as the number of footslips per run for mice that received chondroitinase ABC. The difference between the control and treated mice did not reach statistical significance, but still indicate a moderate behavioral improvement.

In FIG. 9 the activity of chondroitinase ABC was analyzed over the course of 10 days from 10% loaded microspheres. The chondroitinase ABC 10% loaded microspheres were resuspended in PBC. 100 µl aliquots were analyzed daily for CABC activity. The results in FIG. 9 illustrate the sustained and continuous release of CABC from the loaded microspheres over the 10 day test period.

The data from FIG. 8 utilizing sustained release CABC microspheres is indicative that these microspheres can be combined with the Shh microspheres and one or more additional growth factors such as IGF-I or bFGF in order to further improve the SCI niche and provide therapeutic factors enabling growth and/or recovery of damaged neural cells in patients in need of such treatment, as indicated for the mouse SCI models as described herein.

Summary

The present invention demonstrates that transplantation of endothelial-expanded NSCs, which are treated with Shh and retinoic acid, into the dorsal hemisection in a murine model of SCI results in locomotor and sensory recovery (Lowry et al. 2007). Furthermore, a continuous source of Shh at the injury site was provided by incorporating Shh into biodegradable microspheres that were capable of releasing Shh in a sustained manner over the course of at least 7 days. It was demonstrated that Shh provided via biodegradable microspheres is a potent therapeutic agent for treating SCI. Mice that received single injection of Shh-releasing microspheres exhibited motor recovery. This motor recovery is explained, in part, by the decrease in astrocytic scar formation in animals that receive Shh-releasing microspheres, and also by the increased outgrowth of corticospinal tract in these animals. Treatment with a combination of Shh-releasing microspheres and Shh-treated endothelial-expanded cells facilitates the further enhancement of motor recovery. Motor recovery is an aspect of behavioral recovery and can be assessed by behavioral tests. In the present examples, motor recovery refers to locomotion and hind limb movements. Additionally, there was no evidence of tumor formation in any of the treated animals.

Treatment of patients suffering from such degenerative conditions can include the application of Shh, or other exogenous factors which mimic its effects, in order to control, for example, differentiation and apoptotic events which give rise to loss of neurons (e.g. to enhance survival of existing neurons) as well as promote differentiation and repopulation by progenitor cells in the area affected. In preferred embodiments, a source of Shh is a biodegradable microsphere compound releasing Shh. Optionally, this Shh-releasing microsphere compound is administered together with stem cells or endothelial-expanded spinal cord NSCs, which are optionally pre-treated with Shh and/or retinoic acid, to or proximate the area of degeneration.

REFERENCES

Agius, E., C. Soukkarieh, C. Danesin, P. Kan, H. Takebayashi, C. Soula and P. Cochard (2004). "Converse control of oligodendrocyte and astrocyte lineage development by Sonic hedgehog in the chick spinal cord." *Dev Biol* 270(2): 308-21.

Akazawa, C., H. Tsuzuki. Y. Nakamura, Y. Sasaki, K. Ohsaki, S. Nakamura, Y. Arakawa and S. Kohsaka (2004). "The upregulated expression of sonic hedgehog in motor neurons after rat facial nerve axotomy." *J Neurosci* 24(36): 7923-30.

Bambakidis, N. C. and R. H. Miller (2004). "Transplantation of oligodendrocyté precursors and sonic hedgehog results in improved function and white matter sparing in the spinal cords of adult rats after contusion." *Spine J* 4(1): 16-26.

Basso, D. M., L. C. Fisher, A. J. Anderson, L. B. Jakeman, D. M. McTigue and P. G. Popovich (2006). "Basso Mouse Scale for locomotion detects differences in recovery after spinal cord injury in five common mouse strains." *J Neurotrauma* 23(5): 635-59.

Cattaneo, E. M., R (1990). "Proliferation and differentiation of neuronal stem cells regulated by nerve growth factor." *Nature* 347: 762-765.

Charron, F., E. Stein, J. Jeong, A. P. McMahon and M. Tessier-Lavigne (2003). "The morphogen sonic hedgehog is an axonal chemoattractant that collaborates with neurin-1 in midline axon guidance." *Cell* 113(1): 11-23.

Chen, J., S. Y. Leong and M. Schachner (2005). "Differential expression of cell fate determinants in neurons and glial cells of adult mouse spinal cord after compression injury." *Eur J Neurosci* 22(8): 1895-906.

Enzmann, G. U., R. L. Benton, J. F. Talbott, Q. Cao and S. R. Whittemore (2006). "Functional considerations of stem cell transplantation therapy for spinal cord repair." *J Neurotrauma* 23(3-4): 479-95.

Gage, F. (2000). "Mammalian neural stem cells." *Science* 287(5457): 1433-8.

Harel, N. Y. and S. M. Strittmatter (2006). "Can regenerating axons recapitulate developmental guidance during recovery from spinal cord injury?" *Nat Rev Neurosci* 7(8): 603-16.

Jessell, T. M. (2000). "Neuronal specification in the spinal cord: inductive signals and transcriptional codes." *Nat Rev Genet* 1(1): 20-9.

Li, S., J. E. Kim, S. Budel, T. G. Hampton and S. M. Strittmatter (2005). "Transgenic inhibition of Nogo-66 receptor function allows axonal sprouting and improved locomotion after spinal injury." *Mol Cell Neurosci* 29(1): 26-39.

Lowry. N., S. K. Goderie. M. Adamo, P. Lederman, C. Chamiga, J. Gill. J. Silver and S. Temple (2007). "Multipotent embryonic spinal cord stem cells expanded by endothelial factors and Shh/RA promote functional recovery after spinal cord injury." *Exp Neurol.*

Lowry, N. A. and S. Temple (2007). "Making human neurons from stem cells after spinal cord injury." *PLoS Med* 4(2): e48.

Metz, G. A. and I. Q. Whishaw (2002). "Cortical and subcortical lesions impair skilled walking in the ladder rung walking test: a new task to evaluate fore- and hindlimb stepping, placing, and co-ordination." *J Neurosci Methods* 115(2): 169-79.

Palma, V., D. A. Lim, N. Dahmane, P. Sanchez, T. C. Brionne, C. D. Herzberg, Y. Gitton, A. Carleton, A. Alvarez-Buylla and A. Ruiz i Altaba (2005). "Sonic hedgehog controls stem cell behavior in the postnatal and adult brain." *Development* 132(2): 335-44.

Park, E., A. A. Velumian and M. G. Fehlings (2004). "The role of excitotoxicity in secondary mechanisms of spinal cord injury: a review with an emphasis on the implications for white matter degeneration." *J Neurotrauma* 21(6): 754-74.

Qian. X., A. A. Davis, S. K. Goderin and S. Temple (1997). "FGP2 concentration regulates the generation of neurons and glia from multipotent conical stem cells." *Neuron* 18(1): 81-93.

Silver, J. and J. H. Miller (2004). "Regeneration beyond the glial scar." *Nat Rev Neurosci* 5(2): 146-56.

So, P. L., P. K. Yip, S. Bunting, L. F. Wong, N. D. Mazarakis, S. Hall, S. McMahon, M. Maden and J. P. Corcoran (2006). "Interactions between retinoic acid, nerve growth factor and sonic hedgehog signalling pathways in neurite outgrowth." *Dev Biol* 298(1): 167-75.

Sussman, C. R., J. B. Davies and R. H. Miller (2002). "Extracellular and intracellular regulation of oligodendrocyte development: roles of Sonic hedgehog and expression of E proteins." *Glia* 40(1): 55-64.

Tekki-Kessaris, N., R. Woodruff, A. C. Hall, W. Gaffield, S. Kimura, C. D. Stiles. D. H. Rowitch and W. D. Richardson (2001). "Hedgehog-dependent oligodendrocyte lineage specification in the telencephalon." *Development* 128(13): 2545-54.

Thuret, S., L. D. Moon and F. H. Gage (2006). "Therapeutic interventions after spinal cord injury." *Nat Rev Neurosci* 7(8): 628-43.

Vallieres, N., J. L. Berard, S. David and S. Lacroix (2006). "Systemic injections of lipopolysaccharide accelerates myelin phagocytosis during Wallerian degeneration in the injured mouse spinal cord." *Glia* 53(1): 103-13.

Fu K, Harrell R, Zinski K, Um C, Jaklenec A, Frazier J, Lotan N, Burke P, Klibanov A M, Langer R. A potential approach for decreasing the burst effect of protein from PLGA microspheres. *J Pharm Sci* 2003; 92:1582-91.

Lu P. Tuszynski M H (2008). "Growth factors and combinatorial therapies for CNS regeneration." *Exp Neurol*. February; 209(2):313-20.

Ashton, R. S.; Banerjee, A.; Punyani, S.; Schaffer. D. V.; Kane, R. S. (2007) "Scaffolds based on Degradable Alginate Hydrogels and Poly (lactide-co-glycolide) Microspheres for Stem Cell Culture." *Biomaterials*, 28, 36, 5518.

Storkebaum E, Lambrechts D, Dewerchin M, Moreno-Murciano M P, Appelmans S, Oh H, Van Damme P, Rutten B, Man W Y, De Mol M, Wyns S, Manka D, Vermeulen K, Van Den Bosch L. Mertens N, Schmitz C, Robberecht W, Conway E M, Collen D, Moons L, Carmeliet P. Treatment of motoneuron degeneration by intracereebroventricular delivery of VEGF in a rat model of ALS. *Nat Neurosci*. 2005 January; 8(1):85-92. Epub 2004 Nov. 28.

Hashimoto M, Ishii K, Nakamura Y, Watabe K, Kohsaka S, Akazawa C. Neuroprotective effect of sonic hedgehog up-regulated in Schwann cells following sciatic nerve injury. *J Neurochem*. 2008 November; 107(4):918-27. Epub 2008 Sep. 11.

Xu Q G, Midha R, Martinez J A, Guo G F, Zochodne D W. Facilitated sprouting in a peripheral nerve injury. *Neuroscience*. 2008 Apr. 9; 152(4):877-87. Epub 2008 February 15.

Merchán P, Bribián A, Sánchez-Camacho C, Lezameta M, Bovolenta P, de Castro F. Sonic hedgehog promotes the migration and proliferation of optic nerve oligodendrocyte precursors. *Mol Cell Neurosci*. 2007 November; 36(3):355-68. Epub 2007 Aug. 1.

Mastronardi F G, daCruz L A, Wang H, Boggs J. Moscarello M A. The amount of sonic hedgehog in multiple sclerosis white matter is decreased and cleavage to the signaling peptide is deficient. Mult Scler. 2003 August; 9(4):362-71.

Akazawa C, Tsuzuki H, Nakamura Y, Sasaki Y, Ohsaki K, Nakamura S, Arakawa Y, Kohsaka S. The upregulated expression of sonic hedgehog in motor neurons after rat facial nerve axotomy. *J Neurosci*. 2004 Sep. 8; 24(36): 7923-30.

Lu Q R, Sun T, Zhu Z, Ma N, Garcia M, Stiles C D, Rowitch D H. Common developmental requirement for Olig function indicates a motor neuron/oligodendrocyte connection. *Cell*. 2002 Apr. 5; 109(1):75-86.

Sun T, Echelard Y, Lu R, Yuk D I, Kaing S, Stiles C D, Rowitch D H. Olig bHLH proteins interact with homeodomain proteins to regulate cell fate acquisition in progenitors of the ventral neural tube. *Curr Biol*. 2001 Sep. 18; 11(18): 1413-20.

Lu Q R, Yuk D, Alberta J A, Zhu Z, Pawlitzky I, Chan J, McMahon A P, Stiles C D, Rowitch D H. Sonic hedgehog—regulated oligodendrocyte lineage genes encoding bHLH proteins in the mammalian central nervous system. *Neuron*. 2000 February; 25(2):317-29.

Takebayashi H, Nabeshima Y, Yoshida S, Chisaka O, Ikenaka K, Nabeshima Y. The basic helix-loop-helix factor olig2 is essential for the development of motoneuron and oligodendrocyte lineages. *Curr Biol*. 2002 Jul. 9; 12(13): 1157-63.

Zhou Q, Anderson D J. The bHLH transcription factors OLIG2 and OLIG1 couple neuronal and glial subtype specification. *Cell*. 2002 Apr. 5; 109(1):61-73.

Danesin C, Agius E, Escalas N. Ai X, Emerson C, Cochard P, Soula C. Ventral neural progenitors switch toward an oligodendroglial fate in response to increased Sonic hedgehog (Shh) activity: Involvement of Sulfatase I in modulating Shh signaling in the ventral spinal cord. *J Neurosci*. 2006 May 10; 26(19):5037-48.

Yang H, Lu P, McKay H M, Bernot T, Keirstead H, Steward O, Gage F H, Edgerton V R, Tuszynski M H. Endogenous neurogenesis replaces oligodendrocytes and astrocytes after primate spinal cord injury. *J Neurosci*. 2006 Feb. 22; 26(8):2157-66.

Shihabuddin L S, Homer P J. Ray J, Gage F H. Adult spinal cord stem cells generate neurons after transplantation in the adult dentate gyrus. *J Neurosci*. 2000 Dec. 1; 20(23): 8727-35.

Homer P J, Power A B, Kempermann O, Kuhn H G, Palmer T D, Winkler J. Thai L J, Gage F H. Proliferation and differentiation of progenitor cells throughout the intact adult rat spinal cord. *J Neurosci*. 2000 Mar. 15:20(6): 2218-28.

Uchida N, Buck D W, He D, Reitsma M J, Masek M, Phan T V, Tsukamoto A S, Gage F H, Weissman I L. Direct isolation of human central nervous system stem cells. *Proc Natl Acad Sci USA*. 2000 Dec. 19; 97(26):14720-5.

Struve J, Maher P C, Li Y Q, Kinney S, Fehlings M G, Kuntz C 4th, Sherman L S. Disruption of the hyaluronan-based extracellular matrix in spinal cord promotes astrocyte proliferation. Glia. 2005 October; 52(1): 16-24.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the an are deemed to be within the scope of the invention as defined by the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for treating a spinal cord injury in a mammal in need thereof, comprising administering a pharmaceutical formulation comprising poly lactic-co-glycolic acid (PLGA) microspheres and a single active agent consisting of sonic hedgehog (Shh) at the injury site in an amount effective for treating the spinal cord injury, wherein a single administration provides sustained delivery of the Shh for at least 7 days, and wherein an improvement in motor or sensory function is measured after 28 days from initial administration.

2. The method of claim 1, wherein the mammal is a human.

3. The method of claim 1, wherein the pharmaceutical formulation is administered by at least one injection, wherein a first injection is administered at the site of the spinal cord injury.

4. The method of claim 3, wherein a second injection is administered at a site rostral to the site of the spinal cord injury.

5. The method of claim 1, wherein said sustained delivery provides at least 5 ng/ml Shh per day for at least 7 days.

6. A method for increasing neural cell growth or regenerating neural cells in a mammal having spinal cord injury, comprising administering a sustained release pharmaceutical formulation comprising poly lactic-co-glycolic acid (PLGA) microspheres and a single active agent consisting of sonic hedgehog (Shh) at the injury site in an amount effective for increasing neural cell growth or regenerating neural cells, wherein a single administration provides sustained delivery of the Shh for at least 7 days, and wherein an improvement in motor or sensory function is measured after 28 days from initial administration.

7. The method of claim 6, wherein the mammal is a human.

8. The method of claim 6, wherein the neural cell is selected from the group consisting of neurons, glial cells, and progenitor cells.

9. The method of claim 6, which comprises administering at least one injection of the pharmaceutical formulation at a site at which it is desired to increase neural cell growth or regenerate neural cells.

10. The method of claim 9, which comprises administering a second injection of the pharmaceutical formulation at a site at which it is desired to increase neural cell growth or regenerate neural cells.

* * * * *

SEQUENCE LISTING

```
<160> NUMBER OF SEQ ID NOS: 8

<210> SEQ ID NO 1
<211> LENGTH: 462
<212> TYPE: PRT
<213> ORGANISM: Homo sapiens

<400> SEQUENCE: 1

Met Leu Leu Leu Ala Arg Cys Leu Leu Val Leu Val Ser Ser Leu
1               5                   10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
                35                  40                  45

Pro Asn Val Ala Glu Lys Thr Leu Gly Ala Ser Gly Arg Tyr Glu Gly
        50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
                100                 105                 110

Val Met Asn Gln Trp Pro Gly Val Lys Leu Arg Val Thr Glu Gly Trp
            115                 120                 125

Asp Glu Asp Gly His His Ser Glu Glu Ser Leu His Tyr Glu Gly Arg
        130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270
```

```
Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
            290                 295                 300

Phe Ala Ser Arg Val Arg Pro Gly Gln Arg Val Tyr Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
            355                 360                 365

Glu His Ser Trp Ala His Arg Ala Phe Ala Pro Phe Arg Leu Ala His
            370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
            405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
            435                 440                 445

Ser Glu Ala Leu His Pro Leu Gly Met Ala Val Lys Ser Ser
            450                 455                 460

<210> SEQ ID NO 2
<211> LENGTH: 174
<212> TYPE: PRT
<213> ORGANISM: Homo sapiens

<400> SEQUENCE: 2

Cys Gly Pro Gly Arg Gly Phe Gly Lys Arg Arg His Pro Lys Lys Leu
1               5                   10                  15

Thr Pro Leu Ala Tyr Lys Gln Phe Ile Pro Asn Val Ala Glu Lys Thr
            20                  25                  30

Leu Gly Ala Ser Gly Arg Tyr Glu Gly Lys Ile Ser Arg Asn Ser Glu
        35                  40                  45

Arg Phe Lys Glu Leu Thr Pro Asn Tyr Asn Pro Asp Ile Ile Phe Lys
    50                  55                  60

Asp Glu Glu Asn Thr Gly Ala Asp Arg Leu Met Thr Gln Arg Cys Lys
65                  70                  75                  80

Asp Lys Leu Asn Ala Leu Ala Ile Ser Val Met Asn Gln Trp Pro Gly
                85                  90                  95

Val Lys Leu Arg Val Thr Glu Gly Trp Asp Glu Asp Gly His His Ser
            100                 105                 110

Glu Glu Ser Leu His Tyr Glu Gly Arg Ala Val Asp Ile Thr Thr Ser
        115                 120                 125

Asp Arg Asp Arg Ser Lys Tyr Gly Met Leu Ala Arg Leu Ala Val Glu
    130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Ala Lys Ser Gly Gly
                165                 170

<210> SEQ ID NO 3
```

```
<211> LENGTH: 437
<212> TYPE: PRT
<213> ORGANISM: Mus musculus

<400> SEQUENCE: 3

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
    50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
    210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285

Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
        355                 360                 365

Ala His Ala Leu Leu Ala Ala Leu Ala Pro Ala Arg Thr Asp Gly Gly
    370                 375                 380

Gly Gly Gly Ser Ile Pro Ala Ala Gln Ser Ala Thr Glu Ala Arg Gly
```

```
              385                 390                 395                 400
Ala Glu Pro Thr Ala Gly Ile His Trp Tyr Ser Gln Leu Leu Tyr His
                    405                 410                 415

Ile Gly Thr Trp Leu Leu Asp Ser Glu Thr Met His Pro Leu Gly Met
                420                 425                 430

Ala Val Lys Ser Ser
            435

<210> SEQ ID NO 4
<211> LENGTH: 411
<212> TYPE: PRT
<213> ORGANISM: Homo sapiens

<400> SEQUENCE: 4

Met Ser Pro Ala Arg Leu Arg Pro Arg Leu His Phe Cys Leu Val Leu
1               5                   10                  15

Leu Leu Leu Leu Val Val Pro Ala Ala Trp Gly Cys Gly Pro Gly Arg
                20                  25                  30

Val Val Gly Ser Arg Arg Arg Pro Arg Lys Leu Val Pro Leu Ala
            35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Trp Asp Glu Asp Gly His His Ser Glu Glu Ser Leu
    130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Ala Lys Thr Gly Gly Cys Phe Pro Ala Gly Ala
        195                 200                 205

Gln Val Arg Leu Glu Ser Gly Ala Arg Val Ala Leu Ser Ala Val Arg
    210                 215                 220

Pro Gly Asp Arg Val Leu Ala Met Gly Glu Asp Gly Ser Pro Thr Phe
225                 230                 235                 240

Ser Asp Val Leu Ile Leu Leu Asp Arg Glu Pro His Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Thr Ala Asp Asn His Thr Glu Pro Ala Ala
        275                 280                 285

Arg Phe Arg Ala Thr Phe Ala Ser His Val Gln Pro Gly Gln Tyr Val
    290                 295                 300

Leu Val Ala Gly Ala Pro Gly Leu Gln Pro Ala Arg Val Ala Ala Val
305                 310                 315                 320
```

```
Ser Thr His Val Ala Leu Gly Ala Tyr Ala Pro Leu Thr Lys His Gly
            325                 330                 335

Thr Leu Val Val Glu Asp Val Val Ala Ser Cys Phe Ala Ala Val Ala
        340                 345                 350

Asp His His Leu Ala Gln Leu Ala Phe Trp Pro Leu Arg Leu Phe His
            355                 360                 365

Ser Leu Ala Trp Gly Ser Trp Thr Pro Gly Glu Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
            405                 410

<210> SEQ ID NO 5
<211> LENGTH: 437
<212> TYPE: PRT
<213> ORGANISM: Mus musculus

<400> SEQUENCE: 5

Met Leu Leu Leu Leu Ala Arg Cys Phe Leu Val Ile Leu Ala Ser Ser
1               5                   10                  15

Leu Leu Val Cys Pro Gly Leu Ala Cys Gly Pro Gly Arg Gly Phe Gly
            20                  25                  30

Lys Arg Arg His Pro Lys Lys Leu Thr Pro Leu Ala Tyr Lys Gln Phe
        35                  40                  45

Ile Pro Asn Val Ala Glu Lys Thr Leu Gly Ala Ser Gly Arg Tyr Glu
50                  55                  60

Gly Lys Ile Thr Arg Asn Ser Glu Arg Phe Lys Glu Leu Thr Pro Asn
65                  70                  75                  80

Tyr Asn Pro Asp Ile Ile Phe Lys Asp Glu Glu Asn Thr Gly Ala Asp
                85                  90                  95

Arg Leu Met Thr Gln Arg Cys Lys Asp Lys Leu Asn Ala Leu Ala Ile
            100                 105                 110

Ser Val Met Asn Gln Trp Pro Gly Val Lys Leu Arg Val Thr Glu Gly
        115                 120                 125

Trp Asp Glu Asp Gly His His Ser Glu Glu Ser Leu His Tyr Glu Gly
130                 135                 140

Arg Ala Val Asp Ile Thr Thr Ser Asp Arg Asp Arg Ser Lys Tyr Gly
145                 150                 155                 160

Met Leu Ala Arg Leu Ala Val Glu Ala Gly Phe Asp Trp Val Tyr Tyr
                165                 170                 175

Glu Ser Lys Ala His Ile His Cys Ser Val Lys Ala Glu Asn Ser Val
            180                 185                 190

Ala Ala Lys Ser Gly Gly Cys Phe Pro Gly Ser Ala Thr Val His Leu
        195                 200                 205

Glu Gln Gly Gly Thr Lys Leu Val Lys Asp Leu Arg Pro Gly Asp Arg
210                 215                 220

Val Leu Ala Ala Asp Asp Gln Gly Arg Leu Leu Tyr Ser Asp Phe Leu
225                 230                 235                 240

Thr Phe Leu Asp Arg Asp Glu Gly Ala Lys Lys Val Phe Tyr Val Ile
                245                 250                 255

Glu Thr Leu Glu Pro Arg Glu Arg Leu Leu Leu Thr Ala Ala His Leu
            260                 265                 270

Leu Phe Val Ala Pro His Asn Asp Ser Gly Pro Thr Pro Gly Pro Ser
        275                 280                 285
```

```
Ala Leu Phe Ala Ser Arg Val Arg Pro Gly Gln Arg Val Tyr Val Val
    290                 295                 300

Ala Glu Arg Gly Gly Asp Arg Arg Leu Leu Pro Ala Ala Val His Ser
305                 310                 315                 320

Val Thr Leu Arg Glu Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
            340                 345                 350

Ile Glu Glu His Ser Trp Ala His Arg Ala Phe Ala Pro Phe Arg Leu
    355                 360                 365

Ala His Ala Leu Leu Ala Ala Leu Ala Pro Ala Arg Thr Asp Gly Gly
370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
            420                 425                 430

Ala Val Lys Ser Ser
            435

<210> SEQ ID NO 6
<211> LENGTH: 9455
<212> TYPE: DNA
<213> ORGANISM: Homo sapiens

<400> SEQUENCE: 6
gcgaggcagc cagcgaggga gagagcgagc gggcgagccg gagcgaggaa gggaaagcgc      60
aagagagagc gcacacgcac acacccgccg cgcgcactcg cgcacggacc cgcacgggga    120
cagctcggaa gtcatcagtt ccatgggcga gatgctgctg ctggcgagat gtctgctgct    180
agtcctcgtc tcctcgctgc tggtatgctc gggactggcg tgcggaccgg caggggggtt    240
cgggaagagg aggcacccca aaaagctgac ccctttagcc tacaagcagt ttatccccaa    300
tgtggccgag aagaccctag cgccagcgg aaggtatgaa gggaagatct ccagaaactc    360
cgagcgattt aaggaactca cccccaatta caaccccgac atcatattta aggatgaaga    420
aaacaccgga gcgacaggc tgatgactca ggtaggaacc cagcgccggg gcgtggaatg    480
tgtggctttc caggggggtta cgagaagccg aacacttcca gacttaactc tgtttgctct    540
tcgggcagat aggaaggtga tttcacccgc tccttcccca cccacctgcc cgcccccat    600 ctcttcctct tcctggagga gaatggaggt caagggtcca gctggagaag tttagggtgt    660 ggtggggtg aggacggtaa cagacgtggt tcattatggc cctgatttga tgagtcttgc    720
tacaatggcc ttccccatcc tacctctgcc ctggcttgta acttggggag accttcactt    780
tgggggcgtc ggccctttcc aagtcaggag tggaaatgga aggagaggct gggaatcccc    840
ctcccacaaa catgaagtgg tctcctggca ctgtacgaac gaacgaacgt agccttgggc    900
attggagctc agagccccca cgtttcccgt tgcctctgtg gttttctttc ccaccactac    960 ccccacctg cacctccca ccaaagaatt ctcaactgga aaagccagga ggcggttctg   1020
acaaaaggca ggggctccag gggagactcc gcccgtccct gggtggctgg ctgtatcgca   1080
gagctggctt tgcgattgcg tgtccgcaat tgtgccatc agagtgtgaa tgtattgata   1140
tttctttaag gatgctcttt cgttcttcca agcccgaggt accttagggg agggacttag   1200
```

```
aacttattgg cattgcatca ctttagtttt caacctgctt gcataagaat taagagcgaa    1260
taaatattag tgtggggga ggggaagcta agcaaaatat gaattcctct ctctctcccc    1320
acctcctttg agatttctga gctgccaatc tcccagccaa ttctagactt tctgaaactc    1380
catgcacgta taactgaagc cagaaatggg tttccttgca aatataggtc aacatccttt    1440
ttattgccct attaaaatat tcaagtccta cctttagggc taggtgcgta cagcggctga    1500
tggagtggcg ctggtgggc gcaagtgcag ggggaggta ctgacggcag agagaggga     1560 gctacctccg tgccgccctg cttcccgacc cgattcccag gcttgcttga ggccgagaaa    1620
ggcgaggggc aggcaaggta gcctgctcca gctgtcggaa gggagaggaa tgggaaatgg    1680
tcctgatttc cttgctctcc ctcatctgct cccgaccacc ttaaatctgg accgcgagtg    1740
tggacgcgcg cgccagtgcc agacagcagc gcgatccaca attaactctg cacgggccat    1800
ggggtgcccg gtgcgtgcag ctggctggag ggagttctcc ggctagcccg aggcgcccat    1860
cctctcgtca ccctcactcc ccgcggagga ggggccttgc cagggtccct cggaacccga    1920 gaggaggggag gcactgcgga gagagcggcg ggggcgtgga tacccgaggt cccagagcca    1980
gagtgggtca gcttctgccc tgctctgcgg gaggccaata ccgcagaagg ggtcctgggc    2040
tcgcacacct tcccagggct tgggccttgc agccctgctg caaagctgca agcgcacaga    2100
gccgcgcagc gaggcagacg cctgcagccc cacttactcc cgggttatcg atccccgcg     2160 gctagggttt cagtgcgcga ggggctgggc tggagccgcc gggctctgct gctccacgcg    2220
cgggagcgca ggcaccgcag agctaacagc agcgccgggc tcgctgtagt gtccccggcg    2280 gcggggggcgc ggagatgggg gcgccgcgcg aggggccggg gcgcatcgcg ggctccgccg    2340
gcctgccctg ggacgcgccc ccatccccag tccgccgcct gcctggcctc taggcctccg    2400
cgtcccagcc ggagcccca gcccgggggc ctcccccga cccccgtccg ccctgccggg    2460
ggacgcaggg cccagcggcc ccgcgcccgg ccactctcgc cgccgcgcgc acaggcagca    2520
tttgaacttc tgaccttctg tcaacttccc tcagacgaac gaaacgaaaa caaatacttt    2580
tttccttggg cagtggctat tcccgttccc aacacaaaag gaggggaag gacggcccaa     2640 gtggggttg ggtgaggaga gccaggccgg gattatcagg cagaccccac aaaggtcccc    2700
taaaaccgag gggggtaggg gctggcagtc tgtgaggtat ccccggttga tccctcccct    2760
accttccttc tcccgattcc aggagttaag ggtgggggag gaagggatgg ggaaggcgga    2820
ggctcgggtg ctgagggcag gggcgggtg caggaggcgg cagggagcc ccaggccggc     2880 gggaggtttg gggagcctgc tcggccgcc tcatttaaa taaccaccta ggctctgccc    2940
caggtgcgtg accctcttct tctgtctccc tccctgtctc tgggtctcta atgtgactgc    3000
cgcccaagtc cctcaaccat ggcgagatcg tccccagtgg aactttcgga gcagttccgg    3060
aacgcaggag ctgccggtta atattaaccc gggagaggaa agcgcagaca gacacgctct    3120
ccccgcgcgg gcctaggtgc caggcgaggg tgctggcggc cagggggctc ctaaggggca    3180
ggaggccaga gggccggatc tgaagcctgg agtgggtcc cgagccgcta cactaaatag    3240
atttaatgtg cgctctgggg ccgccaggaa agacgctcag gtatgggtt ggggagggc     3300 tgttccacca agcgtggggg aaaggacagt ggagagaggt gcgtttaggg gctggggctg    3360
tcttgaagct gggacgcccc cgccccgcg ctggggaag cccaccggct gctggcggtg     3420
acactcgccg gcgcggctcg cagatcaggg aggtaggcgg gagctcaggc gtggggaaca    3480
acttggcctc cgccgacaca aagcccgcc ccggcggccc tgctgggctt cacggtggct     3540
gcacagagtc gggcttgatt cgcggcacac gacccaatga attaataacc ggcctgggct    3600
```

-continued

```
tcccggctttt gcctgcgaca atcccgccca gcgcgggcgg aggagaggcc gccagccgag      3660
gccgcgcgga gccgggccg gaggagggcg caagggggcgg gggcgccaac tccagcaacc      3720
ctcggcctcc gccccctcact cgcgcagcca cctcccgtcg cggcccggct ggacccgggt      3780
ctccctgccc ggggtcctcc atgcctgccc aagtggcgca gctcacagag ctggggggcca      3840 ggtcatcctc accctgccgc cctctccctg gctgccctcc tgggaagctg tttaaagctt      3900
cttcggcaca gccccagggg agggagctgc ggtggggtgg ggggcttgca tgggggtccc      3960
tgtgcgtgtt ggtggtgtgc gcctgcgcgc aacgggcctc acatcatagc tctacactga      4020
ccctggttta ctgattgatt ttcatgtaaa acgcgttcaa tcctcaagat gacctcactc      4080
aaactctgcc cttccgactt ttttttttaa ctgctggcag gcccacaaac atgcaggcac      4140
tgacctgtta ccagggcggc ccccagccct accccaccccc cagttgttgc atgttgaact      4200
ctacaaccat attactgggt tttattgctg ccagatacac aggacttttc ctgttgcgca      4260
atttgtcacg tcccttaaa gcgccgcagc agtggggcca gcgtcctcgc cccaccctct      4320
cgaaagagtc cccccaaccc acgctacagt tagggccctg gatagaagct gtccctccat      4380
ggcgacaacc agactccaag cagagcatcc ttccagactg gaggaggtta gaggtcagcc      4440
ccgccctctg cagaagtcac cttgaaattg cccctcggcc tccacttggc gcagcttctt      4500 ggggggatgcc accatcgtca tctgtgccag ttccccctct ttaaatcccg tgtcccacca      4560
gcagcagcag ggtaaacatc caggaagcaa gtcagtgccc ccacaaacac acacagtgga      4620
ttcaactgct ttctgtcgca tccttatctg agggtgaccc cagaattcca ggggaaccccc      4680 cacaatctga atcccaggta accccgtctg catctgccta gtcagtgttt cctgcctcct      4740
cccaggcaac ttcctgggaa actcccccagg cggaggactc cgagacctca ggccttcctg      4800
tctcccctcc ccctcctctc aaaccccctcc ccctccctcc acctcttcag tttgctcttc      4860
aaacttgctg gacgccattc tatgctgggg ccaagaacac aagagcggag gaagggaaca      4920
ggttaaagaa aacaagaaac acaatcagac cacagaaaag ccaggcagaa aagggttcga      4980
cgggcaaaaa gaatgtggct gtccagataa agaatgtctg tcccggcccc ggcctgtgct      5040
gcaagtggca actcacctag ccgcctgcca cccaggctcc cgcccaccgc gcagccccgc      5100
cagcggcttc tcgcctcccc tctgcctcgg atagggttag ggcctgaggt aaataaatgc      5160
aaggccttca attctccaag cagtgcgcag tgcatttttc tttatttctg ggaacttgcg      5220
cccaggtctc tgtcaggcct gctgtgaggg attctacgcg gggagaaggt ggaggctgcg      5280
caggtggaga aaggggcccc agaagggggg ctagaagtgg agggcaacgt ggggggcgggg      5340 cgggtatccc agagggtgcc cctggagggt cctgtagttg atgtcttaaa catgcaggtc      5400
acttgtttca gagaaacttt atttgcttct taggcctcgc taggagcatc ggctgtttca      5460
ggacctggag aaaggccccc agctctaccc tgagaggacg tgctcctcca cgctcctccg      5520
caaatgctgt ccctcttccc cagcccaggg cccggctctt cggtgtgtct gggccattcc      5580 aaccccccgtc tccccacctc tccgcatggc cctcgcgcct tgagactggg cagggcaggc      5640
tgatggaggg gccgggaggg gtggcgattg cccaggctaa cgtgtccgtc ggtggggtc      5700 cccttgtctt cgcagaggtg taaggacaag ttgaacgctt tggccatctc ggtgatgaac      5760
cagtggccag gagtgaaact gcgggtgacc gagggctggg acgaagatgg ccaccactca      5820
gaggagtctc tgcactacga gggccgcgca gtggacatca ccacgtctga ccgcgaccgc      5880
agcaagtacg gcatgctggc ccgcctggcg gtggaggccg gcttcgactg ggtgtactac      5940
```

-continued

```
gagtccaagg cacatatcca ctgctcggtg aaagcaggta agctggccct ggcccccgg    6000 atccgaccca aggaaggcca ttggcgcacc tcggcttgat tcaagagaaa aagaaacctg   6060
gggggaggct gagggccagg agcaggggcg ctgggcgatg actgcgtttc cgcggtggaa   6120
cctgccctgt gaggtgccgg cccctcgaaa tcacccctac ctttgaggcc acagagccca   6180
aggttctcca tgccccgaga tggggtcctg tggcttcctg cccgcttctg gagccccac    6240 tgcagggggg gggaaagcgt gactggggga ggggcgctag gcccttccag gcagggaag    6300 acagccctgc gcggttagcc aggtctgggc gagctccttc ctctcgttta gggcttaaga   6360
accaaccgcc cccacccgct atcccaagcg caggggtgtc tatcctgccc cggagcccgc   6420
gtcctggctc ctccccgccg ggcgcccgtg gatcctaagc tgcctttggg gagaggcctg   6480
gtgggcggca gtaaacccag gggcaaccac ctccagcatc tggaggcggc gcgcccggag   6540
cctgcgttcc tactgggagc cgggccggga cgccctgggc ggcgggcagg ccccgaaacg   6600
ccggcccgag tcggcgcgag gctgtcttct ctgggcctgc aacgccacac gctgttgccg   6660
gcgaggaaca gccgtggagg aggcgccatc gcgcgcacgc aaacctccgg cccgaggctg   6720
tgtgcacagc gctcttctcc gcccgcataa attggcacgt ttagcaaagc cgttcacggt   6780
gaatttcggg gaaactctgc cttcctcaac ccccttccag gtttccctac ttgtctccta   6840
aattccatgt taatggcact atgttagtag gaaaacactg ttaaggtgtc aaggcacact   6900
tgtaggtaaa ggctagagtg gcttctcgtc cccacagaaa gcaaaggcgt ggagcggggg   6960
cggcaggggc gggtgtgcgg cccggagagc tcccggctgc aggcaggcag gaggcggcgc   7020
ccccacctcg cgggctcggc ggcggcccct gggcccaggg cgcccctgc gcaaaacctc    7080 ctccccggct ccctgcccgc ggggtccccc tagcggggt ctccggaggc ctcctcccaa    7140
gtgagcagcg ctaatccatc ccccggatcg cgccgggaga cggagccgc ggcgcggag     7200 ccgctcattg gcattctgag cacacgggcg ggggcgcggg gcgcagcgtg tcaagccggg   7260
ccgtgcgact cgacgactcg ggctcgccag cgcccgggt cgcattccgg ggggctacgg    7320
agggcctcca acggccagcc ccgcacttca tgccagagaa accgatgaga agattaaaag   7380
ccccctgtaa ttccagcagg aagattcttt ctggcaatct ctatttgcaa aaagcatgat   7440
cccggagatt ggaatgcaaa aagacggcc ctccccgccc tcctccccgg cccctgcgc    7500 tccgccccaa cttcaattat tgtcctgggg acagtgagcc tcagagagcg acagagggct   7560
cgagaaagcg ggtagtcaag gggccttgag accggcgct tccagcgctc cgaacaggcc    7620
ccgccattta aaattcaaat acacatcttg agtgcttgga agagaggcct ggctgtgcaa   7680
atagtgcttg tgaattgcac acggggtggg ggggggttgc acctgagcaa atagggaggg   7740
ggaggcccgc gagctgggga gagagtgagc tgagaacagg gagggagaa aatgaaagtg    7800 tccccttcca agagtgtctc ctgtttatcc cagaaatcac aatgacaatg ctgggccctt   7860
tattggattt taattagaaa atccacacaa gcctcggatt ttcacacctc ggccaatctc   7920
tggaatgttt gtccagttgc tacaactact gcagctattt ttcactcccc gccccgccc    7980 ctccgcaggc ccacgccgag gcgcggcagg gtgctgcggg caggcgggca ggcgggcagg   8040
cgggccaggt gtttccgccg cgcagcccgg gtgctgagtg cgcgagcagg cgccgcgccc   8100
cgcgccgggg cgggagggaa ggagggtgcg cccggcgccc gcgggagctc aaggaggctt   8160
cctgaggaat ccaagtgcag agcaaacacc tctggatgg attccgcggcg aggccgggtg   8220 tgtgcggagc tgggggtggg gttggaggaa ggcggaagga aagagtgtca ccggcctctg   8280
caggaaacgc cagccaacct ctgtgaccgc cagcccagac ttagagagtc gttaaggaat   8340
```

```
gtgtcggaat cctgtccctg gggcagtggg gttggggggag ggaggtgtgt gcgggacccg    8400
tctggaatca atcgccccgc cccgcgcctt gcgcacccct ggcctaggag cgcgggcacc    8460
aagcgtgcgc cctcctcccc gagacgcgcc tccctctcgg aactcaatgc cctgtcctct    8520
cttctttccc ttctcctcac ccgcagagaa ctcggtggcg gccaaatcgg gaggctgctt    8580
cccgggctcg gccacggtgc acctggagca gggcggcacc aagctggtga aggacctgag    8640 cccccggggac gcgtgctggg cggcggacga ccagggccgg ctgctctaca gcgacttcct    8700
cactttcctg gaccgcgacg acggcgccaa gaaggtcttc tacgtgatcg agacgcggga    8760
gccgcgcgag cgcctgctgc tcaccgccgc gcacctgctc tttgtggcgc gcacaacga    8820 ctcggccacc ggggagcccg aggcgtcctc gggctcgggg ccgccttccg ggggcgcact    8880
ggggcctcgg gcgctgttcg ccagccgcgt gcgcccgggc cagcgcgtgt acgtggtggc    8940
cgagcgtgac ggggaccgcc ggctcctgcc cgccgctgtg cacagcgtga ccctaagcga    9000
ggaggccgcg ggcgcctacg cgccgctcac ggcccagggc accattctca tcaaccgggt    9060
gctggcctcg tgctacgcgg tcatcgagga gcacagctgg gcgcaccggg ccttcgcgcc    9120
cttccgcctg gcgcacgcgc tcctggctgc actggcgccc gcgcgcacgg accgcggcgg    9180
ggacagcggc ggcggggacc gcgggggcgg cggcggcaga gtagccctaa ccgctccagg    9240
tgctgccgac gctccgggtg cgggggccac cgcgggcatc cactggtact cgcagctgct    9300
ctaccaaata ggcacctggc tcctggacag cgaggccctg cacccgctgg gcatggcggt    9360
caagtccagc tgaagccggg gggccggggg agggggcagcg ggaggggggcg ccagctgaag    9420 ccgggggggcc gggggagggg cagcgggagg gggcg                              9455

<210> SEQ ID NO 7
<211> LENGTH: 1314
<212> TYPE: DNA
<213> ORGANISM: Mus musculus

<400> SEQUENCE: 7
atgctgctgc tgctggccag atgttttctg gtgatccttg cttcctcgct gctggtgtgc      60
cccgggctgg cctgtgggcc cggcagggggg tttggaaaga ggcggcaccc caaaaagctg     120 accccttttag cctacaagca gtttattccc aacgtagccg agaagaccct aggggccagc     180
ggcagatatg aagggaagat cacaagaaac tccgaacgat ttaaggaact caccccccaat     240 tacaaccccg acatcatatt taaggatgag gaaaacacgg gagcagaccg gctgatgact     300
cagaggtgca agacaagtt aaatgccttg gccatctctg tgatgaacca gtggcctgga     360
gtgaagctgc gagtgaccga gggctgggat gaggacggcc atcattcaga ggagtctcta     420
cactatgagg tcgagcagt ggacatcacc acgtccgacc gggaccgcag caagtacggc     480
atgctggctc gcctggctgt ggaagcaggt ttcgactggg tctactatga atccaaagct     540
cacatccact gttctgtgaa agcagagaac tccgtggcgg ccaaatccgg cggctgtttc     600
ccgggatccg ccaccgtgca cctggagcag ggcggcacca agctggtgaa ggacttacgt     660 cccgagacc gcgtgctggc ggctgacgac cagggccggc tgctgtacag cgacttcctc     720
accttcctgg accgcgacga aggcgccaag aaggtcttct acgtgatcga gacgctggag     780
ccgcgcgagc gcctgctgct caccgccgcg cacctgctct cgtggcgcc gcacaacgac     840 tcggggccca cgcccgggcc aagcgcgctc tttgccagcc gcgtgcgccc cgggcagcgc     900
gtgtacgtgg tggctgaacg cggcggggac cgccggctgc tgcccgccgc ggtgcacagc     960
```

-continued

| | |
|---|---|
| gtgacgctgc gagaggagga ggcgggcgcg tacgcgccgc tcacggcgca cggcaccatt | 1020 |
| ctcatcaacc gggtgctcgc ctcgtgctac gctgtcatcg aggagcacag ctgggcacac | 1080 |
| cgggccttcg cgcctttccg cctggcgcac gcgctgctgg ccgcgctggc acccgcccgc | 1140 |
| acggacggcg ggggcggggg cagcatccct gcagcgcaat ctgcaacgga agcgaggggc | 1200 |
| gcggagccga ctgcgggcat ccactggtac tcgcagctgc tctaccacat tggcacctgg | 1260 |
| ctgttggaca gcgagaccat gcatcccttg ggaatggcgg tcaagtccag ctga | 1314 |

```
<210> SEQ ID NO 8
<211> LENGTH: 2727
<212> TYPE: DNA
<213> ORGANISM: Mus musculus
```

<400> SEQUENCE: 8

| | |
|---|---|
| acaagctctc cagccttgct accatttaaa atcaggctct ttttgtcttt taattgctgt | 60 |
| ctcgagaccc aactccgatg tgttccgtta ccagcgaccg gcagcctgcc atcgcagccc | 120 |
| cagtctgggt ggggatcgga gacaagtccc ctgcagcagc ggcaggcaag gttatatagg | 180 |
| aagagaaaga gccaggcagc gccagaggga acgaacgagc cgagcgagga agggagagcc | 240 |
| gagcgcaagg aggagcgcac acgcacacac ccgcgcgtac ccgctcgcgc acagacagcg | 300 |
| cggggacagc tcacaagtcc tcaggttccg cggacgagat gctgctgctg ctggccagat | 360 |
| gttttctggt gatccttgct cctcgctgc tggtgtgccc cgggctggcc tgtgggcccg | 420 |
| gcagggggtt tggaaagagg cggcacccca aaaagctgac ccctttagcc tacaagcagt | 480 |
| ttattcccaa cgtagccgag aagaccctag gggccagcgg cagatatgaa gggaagatca | 540 |
| caagaaactc cgaacgattt aaggaactca cccccaatta caaccccgac atcatattta | 600 |
| aggatgagga aaacacggga gcagaccggc tgatgactca gaggtgcaaa acaagttaa | 660 |
| atgccttggc catctctgtg atgaaccagt ggcctggagt gaagctgcga gtgaccgagg | 720 |
| gctgggatga ggacggccat cattcagagg agtctctaca ctatgagggt cgagcagtgg | 780 |
| acatcaccac gtccgaccgg accgcagca agtacggcat gctggctcgc tggctgtgg | 840 |
| aagcaggttt cgactgggtc tactatgaat ccaaagctca catccactgt tctgtgaaag | 900 |
| cagagaactc cgtggcggcc aaatccggcg gctgtttccc gggatccgcc accgtgcacc | 960 |
| tggagcaggg cggcaccaag ctggtgaagg acttacgtcc cggagaccgc gtgctggcgg | 1020 |
| ctgacgacca gggccggctg ctgtacagcg acttcctcac cttcctggac cgcgacgaag | 1080 |
| gcgccaagaa ggtcttctac gtgatcgaga gctggagcc gcgcgagcgc ctgctgctca | 1140 |
| ccgccgcgca cctgctcttc gtggcgccgc acaacgactc ggggcccacg cccgggccaa | 1200 |
| gcgcgctctt tgccagccgc gtgcgccccg gcagcgcgt gtacgtggtg ctgaacgcg | 1260 |
| gcggggaccg ccggctgctg cccgccgcgg tgcacagcgt gacgctgcga gaggaggagg | 1320 |
| cgggcgcgta cgcgccgctc acggcgcacg gcaccattct catcaaccgg gtgctcgcct | 1380 |
| cgtgctacgc tgtcatcgag gagcacagct gggcacaccg ggccttcgcg cctttccgcc | 1440 |
| tggcgcacgc gctgctggcc gcgctggcac ccgcccgcac ggacggcggg ggcgggggca | 1500 |
| gcatccctgc agcgcaatct gcaacggaag cgaggggcgc ggagccgact gcgggcatcc | 1560 |
| actggtactc gcagctgctc taccacattg gcacctggct gttggacagc gagaccatgc | 1620 |
| atcccttggg aatggcggtc aagtccagct gaagcccgac gggaccgggc aaggggcggg | 1680 |
| cggggcgggg agcgactgcg aaataaggaa ctgatgggaa agcgcacgga aggagacttt | 1740 |
| taattataag aataattcat aataataata ataatgataa taataataat aataagtagg | 1800 |

```
gcagtccaaa gtagactata aggaagcaaa aaccccgggg agttctgttg ttatgtttag    1860
tttatatatt tttttgaaat ttttcgttat tgtcttatat gggttgtttt tctcctctcc    1920
tggctattta tttgtttcgt atgaatagat gttttaaaaa tatgaacgga ccttcaagag    1980
ccttaactag tttgtgtctt ggataattta ttattgtgtg aactgtactc acagtgaggg    2040
aaagattatt ttgtgaggcc aagcaacctg ctgaaagtct atttttctac atgtcccttg    2100
tcctgcgttt cagaaggcaa acctccgcat tcctctcctg ctatgctcct gctttcccgc    2160
aagtgtaaac taaaacctgc tccatggggg tccacaaatt atatttttat acacagaatt    2220
gtaaattaga tttttgagag atcaatacct aactgaatga catttcattt tttgaaagtg    2280
taaaatatga aaatatatta ttttaattta actattttcc aatgtaatag ccgtcttctg    2340
tactgccttc ttggtttgta tttgctttgt aaccgccact ttgtcatgtt cttggaaacc    2400
aagactgtta acgcacacat atacactttt tttttttgaca gactggaaga actctgttat    2460
ttttaacttc aaagaattta ttagaaaata atattttttta aaagtgcacc tagcagcgag    2520
cccacgagga tggagcctgt agtttgtaca gagaaaaaca aggatgtttt tgcattaata    2580
aactgagaag taactgctgt aaatttacta aaatgtattt ttgaatattt tgtaatagtt    2640
ttatagaaat aaagcgtgcc acacacaaaa aaaaaaaaaa aaaaaaaaaa aaaaaaaaa    2700 aaaaaaaaaa aaaaaaaaaa aaaaaaa                                       2727
```